United States Patent
King et al.

(10) Patent No.: US 9,609,876 B2
(45) Date of Patent: Apr. 4, 2017

(54) ANTIMICROBIAL COMPOSITIONS

(71) Applicant: DSM IP ASSETS B.V., Heerlen (NL)

(72) Inventors: William Robert King, Echt (NL); Maartje Maria Franse, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/648,363

(22) PCT Filed: Dec. 5, 2013

(86) PCT No.: PCT/EP2013/075688
§ 371 (c)(1),
(2) Date: May 29, 2015

(87) PCT Pub. No.: WO2014/037589
PCT Pub. Date: Mar. 13, 2014

(65) Prior Publication Data
US 2015/0342197 A1  Dec. 3, 2015

Related U.S. Application Data

(60) Provisional application No. 61/734,083, filed on Dec. 6, 2012, provisional application No. 61/734,096, filed on Dec. 6, 2012, provisional application No. 61/734,104, filed on Dec. 6, 2012, provisional application No. 61/734,117, filed on Dec. 6, 2012, provisional application No. 61/734,130, filed on Dec. 6, 2012, provisional application No. 61/734,140, filed on Dec. 6, 2012.

(30) Foreign Application Priority Data

| Jan. 10, 2013 | (EP) | ................................. 13150725 |
| Jan. 10, 2013 | (EP) | ................................. 13150726 |
| Jan. 10, 2013 | (EP) | ................................. 13150727 |
| Jan. 10, 2013 | (EP) | ................................. 13150728 |
| Jan. 10, 2013 | (EP) | ................................. 13150729 |
| Jan. 10, 2013 | (EP) | ................................. 13150730 |

(51) Int. Cl.
| *C07K 14/00* | (2006.01) |
| *A01N 63/02* | (2006.01) |
| *A01N 43/90* | (2006.01) |
| *A01N 37/02* | (2006.01) |
| *A01N 47/44* | (2006.01) |
| *A01N 63/00* | (2006.01) |
| *A23C 19/10* | (2006.01) |
| *A23C 19/11* | (2006.01) |
| *A23L 3/3481* | (2006.01) |
| *A23L 3/3517* | (2006.01) |
| *A23L 3/3571* | (2006.01) |
| *A23L 3/3463* | (2006.01) |
| *A23L 3/3508* | (2006.01) |
| *A23C 19/068* | (2006.01) |

(52) U.S. Cl.
CPC ............. *A01N 63/02* (2013.01); *A01N 37/02* (2013.01); *A01N 43/90* (2013.01); *A01N 47/44* (2013.01); *A01N 63/00* (2013.01); *A23C 19/10* (2013.01); *A23C 19/11* (2013.01); *A23L 3/3481* (2013.01); *A23L 3/34635* (2013.01); *A23L 3/3508* (2013.01); *A23L 3/3517* (2013.01); *A23L 3/3571* (2013.01); *A23C 19/0684* (2013.01)

(58) Field of Classification Search
None
See application file for complete search history.

(56) References Cited

U.S. PATENT DOCUMENTS

| 6,451,365 B1 | 9/2002 | King et al. | |
| 2002/0037260 A1* | 3/2002 | Budny | ..................... A61K 8/64 424/49 |
| 2005/0175594 A1* | 8/2005 | Loessner | .................. A23G 9/30 424/93.6 |

FOREIGN PATENT DOCUMENTS

| DE | 4326617 C1 | 6/1994 |
| EP | 0466244 A1 | 1/1992 |
| WO | 9607756 A1 | 3/1996 |

OTHER PUBLICATIONS

Mora et al.,"Autolytic activity and pediocin-induced lysis in Pediococcus acidilactici and Pediococcus pentosaceus strains", Journal of Applied Microbiology 94: 561-570 (2003).*
International Search Report from PCT/EP2013/075688, mailed Mar. 20, 2015.
Turner, "Antimicrobial activity of lysostaphin and a Listeria monocytogenes bacteriophage endolysin produced and secreted by lactic acid bacterial", Elsevier, ScienceDirect, Systematic and Applied Microbiology 30 (2007), pp. 58-67, XP005816288.
Garcia, "Food biopreservation: promising strategies using pacteriocins, bacteriophages and endolysins", Elsevier, Food Science & Technology, Trends in Food Science & Technology 21 (2010), pp. 373-382, XP027230480.
Celia et al., "Characterization of a bacteriophage lysin (Ply700) from *Streptococcus uberis*." ScienceDirect, veterinary microbiology 130 (2008) 107-117.
Mayer et al., "Molecular Characterization of a Clostridium difficile Bacteriophage and Its CLoned Biologically Active Endolysin." Journal of Bacteriology 190:20 (2008) 6734-6740.
Obeso et al., "Bacteriophage φH5 endolysin activity in milk." (2008).

* cited by examiner

*Primary Examiner* — Anand Desai
(74) *Attorney, Agent, or Firm* — McBee Moore Woodward & Vanik IP, LLC

(57) ABSTRACT

The present invention relates to new antimicrobial compositions and their use in the treatment of products such as food products.

9 Claims, No Drawings

ANTIMICROBIAL COMPOSITIONS

CROSS REFERENCE TO RELATED APPLICATIONS

This application is a §371 National Stage Application of PCT/EP2013/075688, filed 5 Dec. 2013, which claims priority to 61/734,083, filed 6 Dec. 2012, 61/734,096, filed 6 Dec. 2012, 61/734,104, filed 6 Dec. 2012, 61/734,117,filed 6 Dec. 2012, 61/734,130, filed 6 Dec. 2012, 61/734,140, filed 6 Dec. 2012, EP 13150727.9, filed 10 Jan. 2013, 13150730.3, filed 10 Jan. 2013, 13150728.7 filed 10 Jan. 2013, 13150729.5, filed 10 Jan. 2013, 13150726.1, filed 10 Jan. 2013 and 131150725.3, filed 10 Jan. 2013.

BACKGROUND

Field of the Invention

The present invention discloses new antimicrobial compositions to control bacterial diseases and to prevent spoilage of products such as food products.

Description of Related Art

Food-borne diseases are an increasing matter of concern. Recent estimates suggest that about 76 million cases of food-borne illnesses occur annually in the United States alone. 5000 of these cases are reported to result in death.

Microorganisms are the main agents responsible for food spoilage and food poisoning and therefore food preservation procedures are targeted towards them. Food preservation methods currently used by the industry rely either on the inhibition of microbial growth or on microbial inactivation. Examples of procedures for preservation of foods are drying, salting, thermal treatment and fermentation.

Thermal treatment is the most widely used procedure. However, heat can trigger unwanted reactions, leading to undesirable organoleptic and nutritional effects. This limitation together with increasing consumer demand for fresh-like foods has promoted the development of alternative methods for food preservation, among which chemical preservation has been used extensively.

The excessive use of chemical preservatives has resulted in decreasing susceptibility of some microorganisms to these preservatives. Moreover, some of the chemical preservatives are suspect because of their supposed or potential toxicity leading to consumer concern over the possible adverse health effects of these preservatives. As a result thereof, there is an increasing pressure on food manufacturers to completely remove chemical preservatives from their food products and to provide alternatives for preserving food products. The increasing demand for alternatives has opened new dimensions for the use of natural preservatives such as endolysins.

Endolysins are bacteriophage-encoded lytic enzymes that break down the peptidoglycan of the bacterial cell wall during the terminal stage of the bacteriophage reproduction cycle. They have been potential candidate therapeutics for the treatment of bacterial infections of humans and animals and have also been proposed as suitable compounds in the control and detection of microorganisms responsible for food-borne diseases (see Celia et al. (2007), Mayer et al. (2008), and Obeso et al. (2008)).

The use of endolysins however harbours potential risks such as an adverse immune response to either the protein itself or to the release of pro-inflammatory bacterial cell antigens. Next to that, the endolysins may be susceptible for inactivation on or in the food matrix. Moreover, endolysins are expensive to produce and to date have a limited regulatory and consumer acceptance.

Consequently, it can be concluded that there is a severe need for more effective antimicrobial compositions, e.g. antibacterial compositions, for controlling microorganisms responsible for food-borne diseases and preventing spoilage of products, such as food products.

SUMMARY

The present invention solves the problem by providing a new synergistic composition comprising a bacteriophage endolysin and an antimicrobial compound. In an embodiment the antimicrobial compound is an organic acid such as levulinic acid, propionic acid, acetic acid, lactic acid or combinations thereof, but the antimicrobial compound can also be pediocin, nisin, lauric arginate, a lactoperoxidase system, a phage, a sophorolipid or combinations thereof.

The present invention relates to a new synergistic composition comprising a bacteriophage endolysin and a compound selected from the group consisting of pediocin, nisin, levulinic acid, propionic acid, acetic acid, lauric arginate, a lactoperoxidase system, a phage, a sophorolipid and combinations thereof. In an embodiment the composition is a synergistic antimicrobial, e.g. antibacterial, composition. As used herein, the term "synergistic" means that the combined effect of the antimicrobial components when used in combination is greater than their additive effects when used individually.

In the present invention the term "endolysin" has the meaning that is common in the respective technical filed, i.e., denoting enzymes that are naturally encoded by bacteriophages and are produced by them at the end of their life cycle in the host to lyse the host cell and thereby release the progeny phages. Endolysins can also be produced, for instance, recombinantly by heterologous host cells. Endolysins are comprised of at least one enzymatically active domain (EAD) and a non-enzymatically active cell (wall) binding domain (CBD). The EADs can exhibit different enzymatic activities, such as, e.g., N-acetyl-muramoyl-L-alanin amidase, (endo)-peptidase, transglycosylase, glycosyl hydrolase, (N-acetyl)-muramidase, or N-acetyl-glucosaminidase.

DETAILED DESCRIPTION OF A PREFERRED EMBODIMENT

In general, synergy can be calculated as follows: the antimicrobial activity (in %) of the individual active ingredients can be determined by calculating the reduction in bacterial growth observed on/in products treated with the active ingredients in comparison to the bacterial growth on/in products treated with a control composition. The expected antimicrobial activity (E in %) of the combined antimicrobial composition comprising both active ingredients can be calculated according to the Colby equation (Colby, 1967): $E=X+Y-[(X \cdot Y)/100]$, wherein X and Y are the observed antimicrobial activities (in %) of the individual active ingredients X and Y, respectively. If the observed antimicrobial activity (O in %) of the combination exceeds the expected antimicrobial activity (E in %) of the combination and the synergy factor O/E is thus >1.0, the combined application of the active ingredients leads to a synergistic antimicrobial effect.

Pediocins are antimicrobial peptides produced by *Pediococcus* spp. Pediocins are cationic peptides. They contain two structural regions, a highly conserved N-terminal region, that harbors the consensus motif -YGNGV-, and a less conserved C-terminal region. Examples of suitable pediocins are pediocins produced by *P. acidilactici* spp. such as for instance pediocin AcH/PA-1, pediocin L50, pediocin AcM, pediocin F, pediocin SA-1, pediocin SJ-1 and pediocin N5p; pediocins produced by *P. pentosaceus* spp. such as for instance pediocin ST18 and pediocin SM-1; pediocins produced by *P. damnosus* such as for instance pediocin PD-1. However, any other pediocin, not listed above, can also be used. In general, pediocins are known to be active against *Listeria*. They are also active against some other Gram-positive pathogenic bacteria, such as *Clostridium* spp. and *Enterococcus* spp. Pediocin could also be added in the form of a supernatant or fermentate of a starter culture that expresses pediocin.

Nisin is a peptide-like antibacterial substance produced by *Lactococcus lactis* subsp. *lactis*. It comprises about 34 amino acids and is active against mainly gram-positive bacteria. Nisin is non-toxic and is free of side-effects. Nisin is a Generally Recognized as Safe substance. Commercially available nisin products include Delvoplus® and Nisaplin®. The nisin used in the present invention may be nisin A, nisin Z, nisin Q, nisin F, nisin U or a combination thereof.

Levulinic acid (also called 4-oxopentanoic acid) is an organic compound with the formula $CH_3C(O)CH_2CH_2CO_2H$. It is classified as a keto acid. It is relatively non-toxic, with an $LD_{50}$ of 1850 mg/kg. The term levulinic acid as used herein also includes salts and esters of levulinic acid, such as sodium levulinate, calcium levulinate, magnesium levulinate and ethyl levulinate.

Propionic acid (also called propanoic acid) is a naturally occurring carboxylic acid with chemical formula $CH_3CH_2COOH$. The term propionic acid as used herein also includes salts and esters of propionic acid. These are known as propionates (also called propanoates) and include compounds such as sodium propionate, potassium propionate, calcium propionate and methyl propionate.

Acetic acid (also called ethanoic acid) is an organic compound with the chemical formula $CH_3CO_2H$ (also written as $CH_3COOH$ or $C_2H_4O_2$). The term acetic acid as used herein also includes salts and esters of acetic acid. Examples thereof are sodium acetate, calcium acetate, silver acetate, copper acetate, ethyl acetate, n-butyl acetate, isobutyl acetate and propyl acetate. In a preferred embodiment a combination of acetic acid and diacetic acid (also called acetoacetic acid) is used. Diacetic acid is an organic compound with the formula $CH_3C(O)CH_2CO_2H$. The term diacetic acid as used herein also includes salts and esters of diacetic acid such as acetoacetic acid sodium salt and acetoacetic lithium salt.

Lauric arginate ($N^\alpha$-lauroyl-L-arginine ethyl ester monohydrochloride, LAE) is a cationic surfactant, derived from lauric acid, Larginine, and ethanol. LAE is an efficient and broad based preservative, which has a highly efficacious antimicrobial activity against a wide range of food pathogens and spoilage organisms. It has high water solubility (247 g LAE/kg water, partition coefficient between water and oil greater than 10). It is stable and maintains its antimicrobial activity between pH 3-7 and temperatures below 224° F. It has been approved as generally recognized as safe (GRAS) within the United States for certain food applications. The high antimicrobial activity of LAE has been attributed to its action on the cytoplasmic membranes of microorganisms, where it alters their metabolic processes without causing cellular lysis.

A lactoperoxidase system may comprise several components. Suitable lactoperoxidase systems in the light of the present invention can be found in WO 99/022597, WO 91/11105 and WO 97/26908, which are incorporated by reference. The system may comprise a lactoperoxidase (LP; EC 1.11.1.7). In an embodiment lactoperoxidase is present in an amount ranging from 0.1-10,000 mg/l. Lactoperoxidase is an enzyme that is naturally present in milk. The lactoperoxidase in the system can be a milk-derived lactoperoxidase. The lactoperoxidase may for example be of bovine, buffalo, goat, sheep, or camel origin. Methods for isolating lactoperoxidase from milk are known. Alternatively, the lactoperoxidase can be made through recombinant biotechnological methods e.g. by producing the enzyme in a host cell such as a yeast or bacterium. The system may further comprise a halide selected from the group consisting of iodide (I) or bromide (Br) or a salt thereof such as e.g. potassium iodide, sodium iodide, potassium bromide, sodium bromide or a combination thereof. In an embodiment the halide is present in an amount ranging from 0.1-10,000 mg/l. In addition, the system may comprise thiocyanate ($SCN^-$). In an embodiment thiocyanate is present in an amount ranging from 0.1-10,000 mg/l. Thiocyanate can be present in the form of a salt such as e.g. sodium thiocyanate, potassium thiocyanate, ammonium thiocyanate, copper thiocyanate, iron thiocyanate or a combination thereof. In a preferred embodiment the system comprises both a halide as described above and a thiocyanate as described above. The system may also comprise hydrogen peroxide. In an embodiment hydrogen peroxide is present in an amount ranging from 0.1-10,000 mg/l. Hydrogen peroxide may be present as such (e.g. stabilized hydrogen peroxide). Alternatively, a hydrogen peroxide donor system may be present. Suitable hydrogen peroxide donor systems include, but are not limited to, alkali percarbonate (e.g. $2Na_2CO_3 \cdot 3H_2O_2$); earth alkali peroxides (e.g. magnesium peroxide) and other solid peroxides (e.g. carbamide peroxide); systems wherein hydrogen peroxide is produced by oxidation of ascorbic acid; systems wherein hydrogen peroxide is produced by oxidation of glucose by glucose oxidase (E.C. 1.1.3.4); systems wherein hydrogen peroxide is produced by oxidation of hypoxanthine by xanthine oxidase; systems wherein hydrogen peroxide is produced by oxidation of reduced pyridine nucleotides by peroxidase action; or any combination of the previous hydrogen peroxide donor systems.

Suitable phages in the light of the present invention can be found in WO 2004/004495 and WO 2007/093849, which are incorporated by reference.

A sophorolipid is a surface-active glycolipid compound that can be synthesized by a selected number of non-pathogenic yeast species. Sophorolipids are glycolipid class of microbial biosurfactants which consist of a hydrophobic fatty acid tail of 16 or 18 carbon atoms and a hydrophilic carbohydrate head, sophorose. which is a glucose di-saccharide with an unusual β-1,2 bond and can be acetylated on the 6'- and/or 6"-positions. One terminal or sub terminal hydroxylated fatty acid is β-glycosidically linked to the sophorose molecule. The carboxylic end of this fatty acid is either free (acidic or open form) or internally esterified at the 4" or in some rare cases at the 6'- or 6"-position (lactonic form). The hydroxy fatty acid itself counts in general 16 or 18 carbon atoms and can have one or more unsaturated bonds.

The composition of the present invention generally comprises from about 0.001 μg/ml to about 1000 μg/ml and preferably from about 0.01 μg/ml to about 500 μg/ml pediocin and/or nisin. Preferably, the amount is from 0.1 μg/ml to 250 μg/ml. The composition of the present invention generally comprises from about 0.001 µg/ml to about 10,000 µg/ml and preferably from about 0.01 µg/ml to about 5000 µg/ml levulinic acid, propionic acid, acetic acid, sophorolipid and/or lauric arginate. Preferably, the amount is from 0.1 µg/ml to 1000 µg/ml. The composition of the present invention generally comprises from about $10^3$ to $10^{11}$ plaque forming units per ml (pfu/ml) and preferably from about $10^4$ to $10^{10}$ pfu/ml of phage. Preferably, the amount is from $10^5$ to $10^9$ pfu/ml of phage. The composition of the present invention generally comprises from about 0.02 to 2000 units per ml (U/ml) and preferably from about 0.2 to 1000 U/ml of lactoperoxidase system. Preferably, the amount is from 1 to 500 U/ml of lactoperoxidase system.

In an embodiment the bacteriophage endolysin of the present invention is specific for bacteria of at least one genus selected from the group consisting of Listeria, Staphylococcus, Bacillus, Clostridium, Streptococcus, Pseudomonas, E. coli, Klebsiella, Campylobacter, Shigella, Yersinia and Salmonella. In a preferred embodiment the bacteriophage endolysin is specific for bacteria of at least the genus Listeria, i.e. the bacteriophage endolysin is a Listeria bacteriophage endolysin. In a preferred embodiment the bacteriophage endolysin is capable of lysing bacteria of at least one of the above-mentioned genera. In a preferred embodiment the bacteriophage endolysin is capable of lysing at least bacteria of the genus Listeria. In other words, the bacteriophage endolysin of the invention has Listeria endolysin activity. In yet other words, the bacteriophage endolysin of the invention exhibits lytic activity against Listeria bacteria. In a preferred embodiment the bacteriophage endolysin is capable of lysing only bacteria of the genus Listeria. In an embodiment the bacteriophage endolysin provided by the present invention is capable of lysing at least one Listeria serovar selected from the group consisting of serovar 1, serovar 2, serovar 3, serovar 4, serovar 5, serovar 6 and serovar 7. In an embodiment the bacteriophage endolysin is capable of lysing at least two of the above-listed Listeria serovars, preferably at least three of the above-listed Listeria serovars, more preferably at least four of the above-listed Listeria serovars, most preferably at least five of the above-listed Listeria serovars, in particular at least six of the above-listed Listeria serovars and most particularly at least seven of the above-listed Listeria serovars. In an embodiment the bacteriophage endolysin provided by the present invention is capable of lysing at least one Listeria serovar selected from the group consisting of Listeria serovars 1/2a, 1/2b, 1/2c, 1/2d, 3a, 3b, 4a, 4b, 4c, 4d, and 6a. In an embodiment the bacteriophage endolysin is capable of lysing at least two, at least three, at least four, at least five, at least six, at least seven, at least eight, at least nine, at least ten, at least eleven of the above-listed Listeria serovars.

Endolysin activity is analysed by the incubation of killed off Listeria monocytogenes cell suspensions and measuring the decrease in $OD_{600}$ at 30° C. The maximum slope during lyses of the cells is related to the maximum slope corresponding with a known concentration of purified endolysin. For the production of Listeria cells test strains Listeria monocytogenes F2365/ATCC 19117/1E is grown over-night in TB (Terrific Broth: 20 g/L Tryptone, 1 g/L Glucose, 5 g/L NaCl; adjust pH by adding Thiamine HCl) pH 7.3. 500 µl of this culture is used to inoculate 250 ml fresh TB pH 7.3 medium and grown at 30° C. until $OD_{600\ nm}$ of 1.0. After harvesting the cells at 4° C., the supernatant is autoclaved and resuspended in 32 ml PBS buffer pH 8. The supernatant is divided into aliquots of 0.5 ml on ice and the aliquots are subsequently stored at −20° C. (no $N_2$ freezing necessary). Next, 0.5 ml aliquots of Listeria-cells are incubated for 15 minutes at 80° C. and diluted with PBST (Phosphate Buffered Saline with 0.1% Tween 20) to $OD_{600}$ 1.0; subsequently 10 µg/ml DNaseI is added. After pre-warming the samples to 30° C., 990 µl of each sample is applied in cuvettes and the $OD_{600}$ is measured using a spectrophotometer (Jasco "parallel kinetics") for 3 minutes at 30° C. The measurement is continued for another 40 minutes after adding 10 µl of the corresponding protein dilutions.

In the present invention, the genus Listeria encompasses all known Listeria species including, but is not limited to, the following Listeria species: L. monocytogenes, L. seeligeri, L. ivanovii, L. innocua, L. welshimeri, L. grayi ssp. grayi, and L. grayi ssp. murrayi. In the present invention, the preferred Listeria species is a Listeria species that is pathogenic to human beings and/or animals.

In an embodiment the bacteriophage endolysin of the present invention is isolated. The term "isolated" as used herein means an endolysin that is removed from at least one component, e.g. other polypeptide material, with which it is naturally associated (in case of recombinant production "with which it is naturally associated before, during and/or after recombinant production). In other words, the endolysin of the present invention can be isolated, e.g. purified, from a host cell containing or expressing the endolysin by techniques known in the art including, but not limited to, lysis, chromatography, filtration, and centrifugation. An isolated endolysin may contain at most 10%, at most 8%, more preferably at most 6%, more preferably at most 5%, more preferably at most 4%, more preferably at most 3%, even more preferably at most 2%, even more preferably at most 1% and most preferably at most 0.5% as determined by SDS-PAGE of other polypeptide material with which it is natively associated. The isolated endolysin may be free of any other impurities. The isolated endolysin may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9 as determined by SDS-PAGE or any other analytical method suitable for this purpose and known to the person skilled in the art.

In an embodiment the bacteriophage endolysin of the present invention is PlyP40. Information about this endolysin can be found in e.g. WO 2010/010192, which is herewith incorporated by reference. In another embodiment the bacteriophage endolysin of the present invention is PlyP825. Information about this endolysin can be found in e.g. PCT/EP2012/002270, which is herewith incorporated by reference. In another embodiment the bacteriophage endolysin of the present invention is PlyP511. Information about this endolysin can be found in e.g. WO 96/07756, which is herewith incorporated by reference. The nucleotide and amino acid sequences of the above endolysins are shown below.

In an embodiment the bacteriophage endolysin of the present invention is a polypeptide selected from the group consisting of:
(a) a polypeptide comprising an amino acid sequence as set out in SEQ ID NO:2, 4 or 6;
(b) a polypeptide comprising an amino acid sequence having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with the amino acid sequence of SEQ ID NO:2, 4 or 6;

(c) a polypeptide comprising an amino acid sequence having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with the enzymatically active domain of the amino acid sequence of SEQ ID NO:2, 4 or 6, preferably with amino acids 1 to 202 of SEQ ID NO: 2, amino acids 1 to 148 of SEQ ID NO: 4 or amino acids 1 to 182 of SEQ ID NO: 6;

(d) a polypeptide encoded by a polynucleotide comprising the polynucleotide sequence as set out in SEQ ID NO:1, 3 or 5;

(e) a polypeptide encoded by a polynucleotide comprising a polynucleotide sequence having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with the enzymatically active domain coding sequence in SEQ ID NO:1, 3 or 5, preferably having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with the nucleotides 1 to 606 of SEQ ID NO:1, the nucleotides 1 to 444 of SEQ ID NO:3 or the nucleotides 1 to 546 of SEQ ID NO:5;

(f) a polypeptide encoded by a polynucleotide which hybridizes, preferably under at least low stringency conditions, with the complementary strand of SEQ ID NO:1, 3 or 5, preferably with the complementary strand of the enzymatically active domain coding sequence in SEQ ID NO:1, 3 or 5, more preferably with the complementary strand of nucleotides 1 to 606 of SEQ ID NO:1, the complementary strand of nucleotides 1 to 444 of SEQ ID NO:3 or the complementary strand of nucleotides 1 to 546 of SEQ ID NO:5;

(g) a polypeptide encoded by a polynucleotide which hybridizes, preferably under at least low stringency conditions, with the complementary strand of a polynucleotide having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with SEQ ID NO:1, 3 or 5, preferably with the complementary strand of a polynucleotide having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with the enzymatically active domain coding sequence in SEQ ID NO:1, 3 or 5, more preferably with the complementary strand of a polynucleotide having at least 50%, preferably at least 60%, preferably at least 70%, more preferably at least 80%, even more preferably at least 90%, even more preferably at least 93%, even more preferably at least 95%, even more preferably at least 96%, preferably at least 97%, even more preferably at least 98% and even most preferably at least 99% sequence identity with nucleotides 1 to 606 of SEQ ID NO:1, nucleotides 1 to 444 of SEQ ID NO:3 or nucleotides 1 to 546 of SEQ ID NO:5.

(h) a fragment of a polypeptide as defined in (a), (b), (c), (d), (e), (f), or (g), preferably a fragment having an amino acid length of at least 148.

The polypeptide or fragment as defined above under (a) to (h) should be capable of lysing bacteria of the genus *Listeria*. The variants and fragments as defined above under (b) to (h) should still have bacteriophage endolysin activity.

The term "complementary strand" can be used interchangeably with the term "complement". The complement of a nucleic acid strand can be the complement of a coding strand or the complement of a non-coding strand. When referring to double-stranded nucleic acids, the complement of a nucleic acid encoding a polypeptide refers to the complementary strand of the strand encoding the amino acid sequence or to any nucleic acid molecule containing the same.

As used herein, the term "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleotide bases (nucleotides) of the strands of oligomeric compounds. For example, adenine and thymine are complementary nucleic acids which pair through the formation of hydrogen bonds. Hybridization can occur under varying circumstances. "Stringency hybridization" or "hybridizes under low stringency, medium stringency, high stringency, or very high stringency conditions" is used herein to describe conditions for hybridization and washing, more specifically conditions under which an oligomeric compound will hybridize to its target sequence, but to a minimal number of other sequences. So, the oligomeric compound will hybridize to the target sequence to a detectably greater degree than to other sequences. Guidance for performing hybridization reactions can be found in Current Protocols in Molecular Biology, John Wiley & Sons, N.Y. (1989), 6.3.1-6:3.6. Aqueous and non-aqueous methods are described in that reference and either can be used. Stringency conditions are sequence-dependent and will be different in different circumstances. Generally, stringency conditions are selected to be about 5° C. lower than the thermal melting point (Tm) for the oligomeric compound at a defined ionic strength and pH. The Tm is the temperature (under defined ionic strength and pH) at which 50% of an oligomeric compound hybridizes to a perfectly matched probe. Stringency conditions may also be achieved with the addition of destabilizing agents such as formamide. Examples of specific hybridization conditions are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5M sodium phosphate, 7% SDS at 65° C., followed by one or more washes at 0.2×SSC, 1% SDS at 65° C. In general, high stringency conditions, such as high hybridization temperature and optionally low salt concentrations, permit only hybridization between sequences that are highly similar, whereas low stringency conditions, such as low hybridization temperature and optionally high salt concentrations, allow hybridization when the sequences are less similar.

For the purpose of this invention, the term "sequence identity" is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full-length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region. A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp276-277). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity". The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, word length=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used (see the homepage of the National Center for Biotechnology Information).

In another embodiment the bacteriophage endolysin is encoded by a nucleic acid molecule comprising a polynucleotide selected from the group consisting of:

(a) a polynucleotide encoding a polypeptide having the amino acid sequence of SEQ ID NO:2, 4 or 6;

(b) a polynucleotide encoding a fragment, analog or functional derivative of a polypeptide encoded by the polynucleotide of (a), wherein the fragment, analog or functional derivative has *Listeria* endolysin activity;

(c) a polynucleotide comprising the nucleotide sequence of SEQ ID NO:1, 3 or 5;

(d) a polynucleotide comprising part of the nucleotide sequence of (c) and which encodes a fragment, analog or functional derivative of the polypeptide having the amino acid sequence of SEQ ID NO:2, 4 or 6, wherein the fragment, analog or functional derivative has *Listeria* endolysin activity; and (e) a polynucleotide that is the complement of the full length of a polynucleotide of any of (a) to (d).

The polypeptide, fragment, analog of functional derivative encoded by a polynucleotide as defined above under (a) to (e) should be capable of lysing bacteria of the genus *Listeria*.

The term "nucleic acid" as used in the present invention refers to a nucleotide polymer including at least 5 nucleotide units. A nucleic acid refers to a ribonucleotide polymer (RNA), deoxynucleotide polymer (DNA) or a modified form of either type of nucleic acid or synthetic form thereof or mixed polymers of any of the above. Nucleic acids may include either or both naturally-occurring and modified nucleic acids linked together by naturally-occurring and/or non-naturally occurring nucleic acid linkages. The nucleic acid molecules may be modified chemically or biochemically or may contain non-natural or derivatized nucleic acid bases, as will be readily appreciated by those of skill in the art. Such modifications include, for example, labels, methylation, substitution of one or more of the naturally occurring nucleic acids with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The term nucleic acid is also intended to include any topological conformation, including single-stranded (sense strand and antisense strand), double-stranded, partially duplexed, triplex, hairpinned, circular and padlocked conformations. Also included are synthetic molecules that mimic nucleic acids in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers. The term "nucleic acid" and "polynucleotide" can be used interchangeably herein.

The composition of the present invention generally comprises from about 0.1 μg/ml to about 1000 μg/ml and preferably from about 1 μg/ml to about 500 μg/ml bacteriophage endolysin. Preferably, the amount is from 2 μg/ml to 200 μg/ml.

In an embodiment the composition according to the present invention comprises two or more bacteriophage endolysins. Preferably, these endolysins differ, but should at least be capable of lysing bacteria of the genus *Listeria*.

The endolysin of the present invention may be a chimeric protein comprising an endolysin as described herein linked to one or more heterologous proteins or peptides. In various embodiments, the heterologous protein is a heterologous endolysin protein. In various embodiments, the chimeric protein according to the present invention comprises the EAD of an endolysin of the present invention and one or more heterologous proteins. In various embodiments, the chimeric protein as described herein comprises the EAD of a heterologous endolysin and for instance the CBD of the endolysin as described herein. The present invention further provides a chimeric protein comprising an endolysin protein as described herein and one or more lytic domains (i.e., EADs) and/or one or more cell wall binding domains (i.e., CBDs) of other known endolysins from *Listeria* bacteriophages known in the art. The present invention also provides a chimeric protein comprising a lytic domain of the present invention and one or more lytic domains (i.e., EADs) and/or one or more cell wall binding domains (i.e., CBDs) of other known endolysins from *Listeria* bacteriophages known in the art. The present invention also provides a chimeric protein comprising a cell wall binding domain of the present invention and one or more lytic domains (i.e., EADs) and/or one or more cell wall binding domains (i.e., CBDs) of other known endolysins from *Listeria* bacteriophages known in the art. The present invention also provides chimeric proteins comprising the combination of an endolysin of the present invention with autolysins or one or more domains of these autolysins. The present invention also provides chimeric proteins comprising the combination of an endolysin of the present invention with bacteriocins or one or more domains of these bacteriocins. The present invention also provides chimeric proteins comprising the combination of an endolysin of the present invention with one or more antimicrobial peptides. Preferably, the chimeric proteins according to the present invention are capable of lysing bacteria of the genus *Listeria*.

The present invention provides a composition comprising pediocin, an endolysin of the present invention and one or more bacteriophages, preferably known *Listeria*-specific phages, described in the art.

In an embodiment the composition of the present invention further comprises at least one additional compound selected from the group consisting of a sticking agent, a carrier, a colouring agent, a chelating agent, a protective colloid, an adhesive, a herbicide, a fertilizer, a thickening agent, a sequestering agent, a thixotropic agent, a surfactant, a further antimicrobial compound, a detergent, a preservative, a spreading agent, a filler, a spray oil, a flow additive, a mineral substance, a solvent, a dispersant, an emulsifier, a wetting agent, a stabiliser, an antifoaming agent, a buffering agent, an UV-absorber and an antioxidant. In a preferred embodiment the composition of the present invention further comprises at least one additional compound selected from the group consisting of a detergent, a chelating agent and a combination thereof. Examples of chelating agents are EDTA, ascorbic acid, erythorbate. Examples of detergents are Tween, Triton, SLS, Brij. Other destabilizers of membranes can also be used. Of course, the compositions according to the invention may also comprise two or more of any of the above additional compounds. Any of the above mentioned additional compounds may also be combined with the bacteriophage endolysin and/or a compound selected from the group consisting of pediocin, nisin, levulinic acid, propionic acid, acetic acid, lauric arginate, a lactoperoxidase system, a phage, a sophorolipid and combinations thereof in case the bacteriophage endolysin and the compound are applied separately. In an embodiment the additional compounds are additives acceptable for the specific use, e.g. food, feed, medicine, cosmetics or agriculture. Additional compounds suitable for use in food, feed, medicine, cosmetics or agriculture are known to the person skilled in the art.

Compositions according to the invention may have a pH of from 1 to 10, preferably of from 2 to 9, more preferably of from 3 to 8 and most preferably of from 4 to 7. They may be solid, e.g. powder compositions, or may be liquid. The compositions of the present invention can be aqueous or non-aqueous ready-to-use compositions, but may also be aqueous or non-aqueous concentrated compositions/suspensions or stock compositions, suspensions and/or solutions which before use have to be diluted with a suitable diluent such as water or a buffer system. The compositions of the present invention can also have the form of concentrated dry products such as e.g. powders, granulates and tablets. They can be used to prepare compositions for immersion or spraying of products. Of course, the above is also applicable when the bacteriophage endolysin and the compound selected from the group consisting of pediocin, nisin, levulinic acid, propionic acid, acetic acid, lauric arginate, a lactoperoxidase system, a phage, a sophorolipid and combinations thereof are applied as separate compositions.

In a further aspect the invention relates to a kit comprising a bacteriophage endolysin and a compound selected from the group consisting of pediocin, nisin, levulinic acid, propionic acid, acetic acid, lauric arginate, a lactoperoxidase system, a phage, a sophorolipid and combinations thereof. The bacteriophage endolysin and the compound selected from the group consisting of pediocin, nisin, levulinic acid, propionic acid, acetic acid, lauric arginate, a lactoperoxidase system, a phage, a sophorolipid and combinations thereof may be present in at least two separate packages, e.g. containers.

In addition, the kit may comprise a container comprising any of the above-listed additional compounds. The components of the kit may be either in dry form or liquid form in the containers. If necessary, the kit may comprise instructions for dissolving the compounds. In addition, the kit may contain instructions for applying the components. The kit of the present invention generally comprises from about 0.0001 g/l to about 500 g/l of each individual constituent. When a constituent is present in solid form (e.g. as a powder) in the kit, it may be present from 0.01-100%.

As described before, food-borne infections and intoxications caused by contamination of fresh produce, ready-to-eat meats and salads, and other foods continue to increase. By far, the most commonly cited cause of food recalls, as well as the leading cause of death from foodborne infections is due to the bacterial pathogens of the genus *Listeria*, such as for instance *Listeria monocytogenes*. *Listeria monocytogenes* produces mild flu-like symptoms for most victims, but it is of particular concern because of its ability to cause systemic infection (Severe Invasive Listeriosis) in the elderly, the immune compromised, and most alarmingly, pregnant mothers and their unborn infants, resulting in still births and miscarriages.

*Listeria monocytogenes* has unique survival and propagation properties among food pathogens. Unlike other bacterial pathogens such as *Salmonella, E coli*, or *Campylobacter, Listeria monocytogenes* is able to grow robustly at refrigeration temperatures of 4° C. or less. Ergo, refrigeration is not a significant obstacle to this pathogen. This means that a very small amount of contamination on a food product can grow to dangerous levels even under proper refrigeration and handling conditions. *Listeria monocytogenes* is also able to form resistant biofilms on foods and other surfaces, which are extremely difficult to eradicate using normal cleaning and disinfection processes and chemicals. Finally, *Listeria monocytogenes* as a species represents a wide range of serovars, subspecies, and adaptive physiologies that are ideal for survival and growth in a wide range of habitats and conditions. As a result, *Listeria* are often found in a wide range of food processing plants, kitchens, and delis, as well as in a wide range of retail foods, from fresh cantaloupes, lettuce, and cabbage to processed lunchmeats, ready-to-eat deli salads, cheeses, to name just a few.

The first line of defense against *listeria* as well as other pathogens is good sanitation. Unfortunately, it has proven to be virtually impossible to eliminate *Listeria monocytogenes* from most food processing environments. The sanitizing agents used to clean produce and to disinfect food contact surfaces can do part of the job, but they have important limitations. Oxidative disinfectants such as chlorine and ozone are highly reactive with all organic matter, and they are rapidly neutralized by dirt, grease, protein, and other organic materials. A good example is that of vegetable and lettuce processing. Fresh produce typically enters a facility, where it is washed in a flume containing either chlorine or ozone. However, these disinfecting agents are rapidly dissipated by contact with dirt and vegetable pulp, leaving little or no active ingredient to kill the pathogens that may be present. Instead, these pathogens are washed off of an infected head of lettuce and then transmitted via the wash water to thousands of other pieces of lettuce, compounding rather than solving the contamination problem. Use of non-oxidative disinfectants have been tried, but none of these reacts to kill pathogens with the same speed or efficacy, and they all have negative effects on product appearance and flavor. Due to the failure to eliminate environmental *listeria*, foods may carry very low levels of *listeria* through processing, or they may be recontaminated during or after processing but prior to packaging. Contamination may also take place after packaging. There remains an urgent need to kill *listeria* once it is on the food product. Standard food preservation methods typically rely on incorporating hurdles to microbial growth. Examples of procedures for preservation of foods are drying, salting, thermal treatment and fermentation.

For some foods such as hotdogs, salamis, or cured meats, post packaging thermal treatments are sometimes used. However, this is an expensive option, and heat can trigger undesirable organoleptic effects, colour changes, or nutritional losses. This limitation together with increasing consumer demand for fresh-like foods has created opportunities for the use of natural preservatives such as endolysins.

In an embodiment the invention pertains to a method for protecting a product against bacteria, such as bacteria of the genus *Listeria*, by treating the product with a bacteriophage endolysin and a compound selected from the group consisting of pediocin, nisin, levulinic acid, propionic acid, acetic acid, lauric arginate, a lactoperoxidase system, a phage, a sophorolipid and combinations thereof. In addition, the product can be treated with other antimicrobial compounds either prior to, concomitant with or after treatment of the products with a bacteriophage endolysin and a compound selected from the group consisting of pediocin, nisin, levulinic acid, propionic acid, acetic acid, lauric arginate, a lactoperoxidase system, a phage, a sophorolipid and combinations thereof. The product can also be treated with sonication, high pressure, pulse electric field (PEF), irradiation, and/or ultraviolet light either prior to, concomitant with or after treatment of the products with a bacteriophage endolysin and a compound selected from the group consisting of pediocin, nisin, levulinic acid, propionic acid, acetic acid, lauric arginate, a lactoperoxidase system, a phage, a sophorolipid and combinations thereof. This could enhance the speed and efficacy of the treatment with a bacteriophage endolysin and a compound selected from the group consisting of pediocin, nisin, levulinic acid, propionic acid, acetic acid, lauric arginate, a lactoperoxidase system, a phage, a sophorolipid and combinations thereof. The product may be treated by sequential application of a bacteriophage endolysin and a compound selected from the group consisting of pediocin, nisin, levulinic acid, propionic acid, acetic acid, lauric arginate, a lactoperoxidase system, a phage, a sophorolipid and combinations thereof or vice versa. Alternatively, the product may be treated by simultaneous application of a bacteriophage endolysin and a compound selected from the group consisting of pediocin, nisin, levulinic acid, propionic acid, acetic acid, lauric arginate, a lactoperoxidase system, a phage, a sophorolipid and combinations thereof. In case of simultaneous application, the bacteriophage endolysin and the compound selected from the group consisting of pediocin, nisin, levulinic acid, propionic acid, acetic acid, lauric arginate, a lactoperoxidase system, a phage, a sophorolipid and combinations thereof can be present in different compositions that are applied simultaneously or the bacteriophage endolysin and the compound selected from the group consisting of pediocin, nisin, levulinic acid, propionic acid, acetic acid, lauric arginate, a lactoperoxidase system, a phage, a sophorolipid and combinations thereof may be present in a single composition. In yet another embodiment the product may be treated by separate or alternate modes of applying the bacteriophage endolysin and the compound selected from the group consisting of pediocin, nisin, levulinic acid, propionic acid, acetic acid, lauric arginate, a lactoperoxidase system, a phage, a sophorolipid and combinations thereof. In an embodiment the invention is directed to a process for the treatment of products by applying a bacteriophage endolysin and a compound selected from the group consisting of pediocin, nisin, levulinic acid, propionic acid, acetic acid, lauric arginate, a lactoperoxidase system, a phage, a sophorolipid and combinations thereof to the products. In an embodiment the invention pertains to a method for making a product comprising adding a bacteriophage endolysin and a compound selected from the group consisting of pediocin, nisin, levulinic acid, propionic acid, acetic acid, lauric arginate, a lactoperoxidase system, a phage, a sophorolipid and combinations thereof to the product. The invention also pertains to a method for controlling bacterial, e.g. *Listeria*, contamination, preferably for sanitizing and/or disinfecting bacterial contamination, comprising applying a bacteriophage endolysin and a compound selected from the group consisting of pediocin, nisin, levulinic acid, propionic acid, acetic acid, lauric arginate, a lactoperoxidase system, a phage, a sophorolipid and combinations thereof to the site of bacterial contamination, with the proviso that the method is not a therapeutic method. Adding and applying the bacteriophage endolysin and the compound selected from the group consisting of pediocin, nisin, levulinic acid, propionic acid, acetic acid, lauric arginate, a lactoperoxidase system, a phage, a sophorolipid and combinations thereof can be done in various ways as described above. By adding or applying a bacteriophage endolysin and a compound selected from the group consisting of pediocin, nisin, levulinic acid, propionic acid, acetic acid, lauric arginate, a lactoperoxidase system, a phage, a sophorolipid and combinations thereof, bacterial growth on or in the products can be prevented and the product is protected from bacteria, such as bacteria from the genus *Listeria*. In other words, the bacteriophage endolysin and the compound selected from the group consisting of pediocin, nisin, levulinic acid, propionic acid, acetic acid, lauric arginate, a lactoperoxidase system, a phage, a sophorolipid and combinations thereof protect the products from bacterial growth and/or from bacterial infection and/or from bacterial spoilage. The bacteriophage endolysin and the compound selected from the group consisting of pediocin, nisin, levulinic acid, propionic acid, acetic acid, lauric arginate, a lactoperoxidase system, a phage, a sophorolipid and combinations thereof can also be used to treat products that have been infected with a bacterium. By adding or applying the bacteriophage endolysin and the compound selected from the group consisting of pediocin, nisin, levulinic acid, propionic acid, acetic acid, lauric arginate, a lactoperoxidase system, a phage, a sophorolipid and combinations thereof, the disease development due to bacteria on or in these products can be slowed down, stopped or the products may even be cured from the disease. In an embodiment of the invention the products are treated with a composition or kit according to the invention. In an embodiment the product is a food, feed, pharmaceutical, cosmetic or agricultural product. In a preferred embodiment the product is a food product. The product may also be a solid surface such as a (food) package, a (food) storage container, (food) processing equipment, a (food) processing plant, a surface coming into contact with food such as a shelve or a knife, a medical device, to name just a few.

The bacteriophage endolysin and the compound selected from the group consisting of pediocin, nisin, levulinic acid, propionic acid, acetic acid, lauric arginate, a lactoperoxidase system, a phage, a sophorolipid and combinations thereof, the compositions according to the invention and the kits according to the invention can be applied to the products by spraying. Other methods suitable for applying the bacteriophage endolysin and the compound selected from the group consisting of pediocin, nisin, levulinic acid, propionic acid, acetic acid, lauric arginate, a lactoperoxidase system, a phage, a sophorolipid and combinations thereof, the compositions and the kits in liquid form to the products are also a part of the present invention. These include, but are not limited to, dipping, watering, drenching, introduction into a dump tank, vaporizing, rinsing, atomizing, fogging, fumigating, painting, brushing, misting, dusting, foaming, spreading-on, packaging and coating. Spraying applications using automatic systems are known to reduce the labour costs and are cost-effective. Methods and equipment well-known to a person skilled in the art can be used for that purpose. The bacteriophage endolysin and the compound selected from the group consisting of pediocin, nisin, levulinic acid, propionic acid, acetic acid, lauric arginate, a lactoperoxidase system, a phage, a sophorolipid and combinations thereof can be sprayed more than once if needed.

Depending on the type of application, the amount of bacteriophage endolysin applied may vary from 0.1-200 µg/ml, including the range of about 1-10 µg/ml and 0.5-5 µg/ml. In various embodiments, the concentration is contemplated to be in the range of about 1-5 µg/ml, 5-10 µg/ml, or 10-20 µg/ml. In various other embodiments, the concentration is contemplated to be in the range of about 20-40 µg/ml, 40-60 µg/ml, 60-80 µg/ml, 80-100 µg/ml, 100-120 µg/ml, 120-140 µg/ml, 140-160 µg/ml, 160-180 µg/ml or 180-200 µg/ml.

Depending on the type of application, the amount of the compound selected from the group consisting of pediocin, nisin, levulinic acid, propionic acid, acetic acid, lauric arginate, a lactoperoxidase system, a phage, a sophorolipid and combinations thereof applied may vary. Pediocin and/or nisin may be applied from about 0.001 µg/ml to about 1000 µg/ml and preferably from about 0.01 µg/ml to about 500 µg/ml pediocin and/or nisin. Preferably, the amount is from 0.1 µg/ml to 250 µg/ml. Levulinic acid, propionic acid, acetic acid, sophorolipid and/or lauric arginate may be applied from about 0.001 µg/ml to about 10,000 µg/ml and preferably from about 0.01 µg/ml to about 5000 µg/ml. Preferably, the amount is from 0.1 µg/ml to 1000 µg/ml. Phage may be applied from about $10^3$ to $10^{11}$ plaque forming units per ml (pfu/ml) and preferably from about $10^4$ to $10^{10}$ pfu/ml. Preferably, the amount is from $10^5$ to $10^9$ pfu/ml. Lactoperoxidase system may be applied from about 0.02 to 2000 units per ml (U/ml) and preferably from about 0.2 to 1000 U/ml. Preferably, the amount is from 1 to 500 U/ml.

Another aspect of the present invention relates to the use of a bacteriophage endolysin and a compound selected from the group consisting of pediocin, nisin, levulinic acid, propionic acid, acetic acid, lauric arginate, a lactoperoxidase system, a phage, a sophorolipid and combinations thereof to protect a product against bacteria. As indicated above, the bacteriophage endolysin and the compound selected from the group consisting of pediocin, nisin, levulinic acid, propionic acid, acetic acid, lauric arginate, a lactoperoxidase system, a phage, a sophorolipid and combinations thereof may be used, e.g. applied, sequentially or simultaneously. In an embodiment the invention relates to a use, wherein a composition or kit according to the invention is applied to the product. In an embodiment the product is a food, feed, pharmaceutical, cosmetic or agricultural product. In a preferred embodiment the product is food product. The product may also be a solid surface such as a (food) package, a (food) storage container, (food) processing equipment, a (food) processing plant, a surface coming into contact with food such as a shelve or a knife, a medical device, to name just a few.

In a specific embodiment the bacteriophage endolysin and the compound selected from the group consisting of pediocin, nisin, levulinic acid, propionic acid, acetic acid, lauric arginate, a lactoperoxidase system, a phage, a sophorolipid and combinations thereof can be used in medicine, e.g. to treat and/or prevent bacterial diseases. The bacteriophage endolysin and the compound selected from the group consisting of pediocin, nisin, levulinic acid, propionic acid, acetic acid, lauric arginate, a lactoperoxidase system, a phage, a sophorolipid and combinations thereof can for instance be used in the form of a pharmaceutical composition. The composition may further comprise pharmaceutically acceptable excipients. The bacteriophage endolysin and the compound selected from the group consisting of pediocin, nisin, levulinic acid, propionic acid, acetic acid, lauric arginate, a lactoperoxidase system, a phage, a sophorolipid and combinations thereof may be administered orally or parenterally. The type of composition is dependent on the route of administration.

A further aspect of the invention is directed to a product treated with a bacteriophage endolysin and a compound selected from the group consisting of pediocin, nisin, levulinic acid, propionic acid, acetic acid, lauric arginate, a lactoperoxidase system, a phage, a sophorolipid and combinations thereof. In an embodiment the product is treated with a composition or kit according to the invention. The invention is therefore directed to a product comprising a bacteriophage endolysin and a compound selected from the group consisting of pediocin, nisin, levulinic acid, propionic acid, acetic acid, lauric arginate, a lactoperoxidase system, a phage, a sophorolipid and combinations thereof. The treated products may comprise a bacteriophage endolysin and a compound selected from the group consisting of pediocin, nisin, levulinic acid, propionic acid, acetic acid, lauric arginate, a lactoperoxidase system, a phage, a sophorolipid and combinations thereof on their surface and/or inside the product. Alternatively, the treated products may comprise a coating comprising a bacteriophage endolysin and a compound selected from the group consisting of pediocin, nisin, levulinic acid, propionic acid, acetic acid, lauric arginate, a lactoperoxidase system, a phage, a sophorolipid and combinations thereof. In an embodiment the product is a food, feed, pharmaceutical, cosmetic or agricultural product. In a preferred embodiment the product is a food product. The product may also be a solid surface such as a (food) package, a (food) storage container, (food) processing equipment, a (food) processing plant, a surface coming into contact with food such as a shelve or a knife, a medical device, to name just a few.

The term "food products" as used herein is to be understood in a very broad sense and includes, but is not limited to, dairy products, meat products, fish products, beverage products, baking products, unpasteurized food products, salads, and sauces, marinades, salsas and seasonings.

As used herein, the term "dairy product" is intended to include any food product made using milk or milk products, including, but not limited to, milk, yoghurt, ice cream, cheese, skimmed milk, acidified milk, butter milk, condensed milk, spreads, margarines, milk powder, butter, EMC (Enzyme Modified Cheese), dulche de leche, coffee whitener; coffee creamer, cream, sour cream, ghee, and dairy analogue. Cheese may be any kind of cheese, e.g. fresh cheese, hard cheese, curd cheese, cream cheese, white mould cheese, blue mould cheese and process cheese. The term 'analogue of a dairy product' or 'dairy analogue' refers to a dairy-like product which contains a dairy composition as defined herein and which composition comprises at least one analogue of a dairy ingredient. In various embodiments, the milk is raw milk or milk that has been pasteurized.

As used herein, the term "meat product" is intended to include any food product, which contains animal tissue, including, but not limited to, beef, pork, and poultry. The term "ready-to-eat meat product" is intended to include any meat product, which does not require cooking prior to consumption, including, but not limited to, pates, hot dogs, bologna, ham, salami, sausages, deli meats, and cold cuts.

As used herein, the term "fish product" is intended to include any food product, which contains tissue from an aquatic animal, including, but not limited to, lobster, crab, fresh water, smoked salmon, smoked other fish, salted fish, saltwater fish and other seafood.

As used herein, the term "beverage product" is intended to include ready-to-drink compositions as well as concentrates comprising water and at least one other ingredient and includes, but is not limited to, carbonated and non-carbonated soft drinks, carbonated and non-carbonated water compositions, fountain beverage compositions, frozen ready-to-drink beverage compositions, coffee beverage compositions, decaffeinated coffee beverage compositions, tea beverage compositions (from regular tea, tea derived from fruit products, tea derived from herb products, or decaffeinated tea), dairy beverage compositions, beverage compositions comprising milk derived from soy, rice, coconut or other plant material, powdered soft drinks, vitamin-enhanced soft drinks, liquid concentrated beverage compositions, flavored water compositions, enhanced water compositions, juice compositions (juice derived from any fruit or any combination of fruits and/or juice derived from any vegetable or any combination of vegetables), juice-flavored drinks (juice derived from any fruit or any combination of fruits, juice derived from any vegetable or any combination of vegetables), nectar beverage compositions, sport drinks, highly caffeinated high energy drinks, non-alcoholic beer or wine compositions, and alcoholic beverage compositions (e.g. wine, champagne, malt liquor, rum, gin, vodka, other hard liquors, beer, reduced calorie beer-type beverages, and other beer-type beverages obtained from a cereal solution such as beer, ale, stout, lager, porter, low alcoholic beer, kvass, rye-bread beer, shandy, and malt drinks). If in the form of a concentrate, beverage products suitable for consumption can be prepared by adding volumes of water to the concentrate. Typically, beverage products suitable for consumption can be prepared from the concentrates by combining approximately 1 part concentrate with between approximately 3 to approximately 7 parts water. In general, water is the basic ingredient of the beverage products disclosed herein, typically being the vehicle or liquid portion in which the remaining ingredients are dissolved, emulsified, suspended or dispersed. Purified water can be used in the manufacture of certain embodiments of the beverages disclosed here, and water of a standard beverage quality can be employed in order not to adversely affect beverage taste, odor, or appearance. The water typically will be clear, colorless, free from objectionable minerals, tastes and odors, free from organic matter, low in alkalinity and of acceptable microbiological quality based on industry and government standards applicable at the time of producing the beverage product. Moreover, beverage products may comprise one or more additional additives selected from anti-foaming agents, flavors, clouding agents, coloring agents, thickening agents, vitamins, amino acids, minerals, foaming agents, hydrocolloids, herbs, neutraceutical compounds, acidity regulators, preservatives, polysaccharides, sweetening agents, emulsifiers, antioxidants, dietary fibers, bacterial cultures, mono- and polynucleotides, polypeptides, enzymes and mixtures thereof. Each of these materials may be a single component or a mixture of two or more components.

As used herein, the term "baking product" is intended to include any product prepared from a dough or a batter. The product may have a soft or a crisp character and may be of a white, light or dark type. Baked products include, but are not limited to, bread such as for instance white, whole-meal or rye bread, French baguette-type bread, laminated dough products such as (Danish) pastry, croissants or puff pastry, pita bread, tortillas, tacos, cakes, pancakes, biscuits, cookies, doughnuts, bagels, pie crusts, muffins, steamed bread, and crisp bread. Types of baked products, methods to characterize and to produce them are known to those skilled in the art see for example "Baking Science and Technology", by E. J. Pyler, L. A. Gorton, 2008, (2 volumes) Sosland Publishing Company, Kansas, USA, or "Baked Products: Science, Technology and Practice" by S. P. Cauvain, L. S. Young, 2006, Blackwell Publishing Ltd, Oxford, UK. As used herein, the term "unpasteurized food product" is intended to include any food product, whereby at least one ingredient is unpasteurized and which does not undergo a final heat treatment.

As used herein, the term "salad" is intended to include any food product, which contains vegetables, fruits or mixtures thereof. Examples include, but are not limited to, products that are presented for consumers to choose from in a display commonly referred to as a "salad bar", deli salads, processed fruit and vegetables, cut salads and cut vegetables such as cut lettuce, cut romaine lettuce, cut spinach and cut endive. Of course, the salads can also be uncut.

The term "feed products" as used herein is also to be understood in a very broad sense and includes, but is not limited to, pet food, broiler feed, etc.

The term "pharmaceutical product" as used herein is also to be understood in a very broad sense and includes products comprising an active molecule such as a drug, agent, or pharmaceutical compound and optionally a pharmaceutically acceptable excipient, i.e. any inert substance that is combined with the active molecule for preparing an agreeable or convenient dosage form.

The term "cosmetic product" as used herein is also to be understood in a very broad sense and includes products that are used for protecting or treating horny tissues such as skin and lips, hair and nails from drying by preventing transpiration of moisture thereof and further conditioning the tissues as well as giving good appearance to these tissues. Products contemplated by the term "cosmetic product" include, but are not limited to, moisturizers, personal cleansing products, occlusive drug delivery patches, nail polish, powders, wipes, hair conditioners, skin treatment emulsions, shaving creams and the like.

The term "agricultural products" as used herein is also to be understood in a very broad sense and includes, but is not limited to, cereals, e.g. wheat, barley, rye, oats, rice, sorghum and the like; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes, aubergines; fibrous plants, e.g. cotton, flax, hemp, jute; citrus fruit, e.g. oranges, lemons, grapefruits, mandarins, limes; tropical fruit, e.g. papayas, passion fruit, mangos, carambolas, pineapples, bananas, kiwis; vegetables, e.g. spinach, lettuce, asparagus, brassicaceae such as cabbages and turnips, carrots, onions, tomatoes, potatoes, seed-potatoes, hot and sweet peppers; laurel-like plants, e.g. avocado, cinnamon, camphor tree; or products such as maize, tobacco, nuts such as pistachio nuts, peanuts and cashew nuts, coffee beans, sugarcane, tea, grapevines, hops, rubber plants, as well as ornamental plants, e.g. cut flowers, roses, tulips, lilies, *narcissus*, crocuses, hyacinths, dahlias, *gerbera*, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables.

A method for preparing a composition as described herein is another aspect of the present invention. The method comprises adding a bacteriophage endolysin to a compound selected from the group consisting of pediocin, nisin, levulinic acid, propionic acid, acetic acid, lauric arginate, a lactoperoxidase system, a phage, a sophorolipid and combinations thereof or vice versa. The bacteriophage endolysin and the compound selected from the group consisting of pediocin, nisin, levulinic acid, propionic acid, acetic acid, lauric arginate, a lactoperoxidase system, a phage, a sophorolipid and combinations thereof may for instance be added separately to an aqueous composition and mixed, followed, if necessary, by adjustment of the pH, viscosity, etc. If added separately, some or all of the separate components may be in powder form, but alternatively some or all may also be in liquid form. The bacteriophage endolysin and the compound selected from the group consisting of pediocin, nisin, levulinic acid, propionic acid, acetic acid, lauric arginate, a lactoperoxidase system, a phage, a sophorolipid and combinations thereof may for instance also be added to one another in powder form and mixed to obtain a powdered composition. The powdered composition may then be added to an aqueous composition.

A method of producing a kit as described herein is another aspect of the present invention. The method comprises the steps of:
(a) providing a bacteriophage endolysin according to the present invention, optionally comprised within a suitable packaging unit;
(b) providing a compound selected from the group consisting of pediocin, nisin, levulinic acid, propionic acid, acetic acid, lauric arginate, a lactoperoxidase system, a phage, a sophorolipid and combinations thereof, optionally comprised within a suitable component packaging unit;
(c) optionally providing a suitable kit packaging unit;
(d) optionally placing the bacteriophage endolysin of step (1) and the compound selected from the group consisting of pediocin, nisin, levulinic acid, propionic acid, acetic acid, lauric arginate, a lactoperoxidase system, a phage, a sophorolipid and combinations thereof of step (2) within the packaging unit wherein the bacteriophage endolysin of step (1) and the compound selected from the group consisting of pediocin, nisin, levulinic acid, propionic acid, acetic acid, lauric arginate, a lactoperoxidase system, a phage, a sophorolipid and combinations thereof of step (2) are physically separated within the kit packaging unit;
(e) optionally providing instructions for using the kit.

The nucleotide and amino acid sequence of the bacteriophage endolysins PlyP40, PlyP825 and PlyP511 are:

```
(nucleotide sequence of
wild-type bacteriophage endolyin PlyP40)
                                   SEQ ID NO: 1
ATGGCGTTAGTTTTAGACATTTCAAAATGGCAACCGACAGTGAATTATTC

AGGACTAAAAGAAGATGTAGGATTCGTTGTCATTCGTTCTAGCAACGGAA

CACAGAAGTATGATGAGAGATTAGAGCAACACGCAAAAGGCTTAGATAAA

GTGGGAATGCCTTTCGGACTGTACCACTACGCTTTATTTGAAGGTGGACA

AGATACTATCAATGAAGCGAATATGTTAGTTAGCGCATATAAGAAATGTC
```

-continued

```
GTCAATTAGGCGCAGAACCAACATTCTTGTTCTTAGATTATGAAGAAGTC

AAGTTAAAATCTGGTAATGTGGTAAACGAATGTCAGAGATTTATAGACCA

TGTGAAAGGTCAAACTGGGGTCAAAGTAGGACTTTATGCTGGGGATAGTT

TTTGGAAGACGCACGATTTAGATAAAGTCAAGCACGATTTAAGATGGGTA

GCTAGATATGGGGTAGATAACGGTAAACCGTCTACAAAACCATCTATACC

TTATGATTTGTGGCAGTATACTTCCAAGGGGCGAATTAAAGCCATTGCTT

CACCTGTAGATATGAATACATGTTCTAGCGACATATTGAACAAATTAAAA

GGTTCAAAAGCACCTGTTAAACCAGCACCAAAACCGACACCTAGTAAGCC

AGCACCAGCGAAACCAGCACCAAAAACGACTACTAAATATGTCAATACGG

CACATTTAAATATTCGTGAAAAGGCAAGTGCTGACTCGAAAGTATTGGGA

GTTCTTGACCTAACGATTCCGTACAGGTCATTTCTGAATCAGGTGGATG

GTCTAAGTTGAAATCTGGGAACAAGCAAGTATATGTTTCTAGCAAGTATC

TTAGTAAGTCAAAAACGACACCGAAGGCGAAACCAAGCTCGAAACAGTAT

TATACTATTAAAAGCGGTGATAATTTAAGTTACATTGCTAAGAAGTATAA

AACTACAGTAAAACAGATTCAAAACTGGAACGGTATCAAGGATGCTAACA

AAATTTACGCAGGTCAAAAAATTAGAGTTAAATAA
```

(polypeptide sequence of bacteriophage endolyin PlyP40; underlined is the EAD of the endolysin)
SEQ ID NO: 2

<u>MALVLDISKWQPTVNYSGLKEDVGFVVIRSSNGTQKYDERLEQHAKGLDK</u>
<u>VGMPFGLYHYALFEGGQDTINEANMLVSAYKKCRQLGAEPTFLFLDYEEV</u>
<u>KLKSGNVVNECQRFIDHVKGQTGVKVGLYAGDSFWKTHDLDKVKHDLRWV</u>
<u>ARYGVDNGKPSTKPSIPYDLWQYTSKGRIKAIASPVDMNTCSSDILNKLK</u>
GSKAPVKPAPKPTPSKPAPAKPAPKTTTKYVNTAHLNIREKASADSKVLG
VLDLNDSVQVISESGGWSKLKSGNKQVYVSSKYLSKSKTTPKAKPSSKQY
YTIKSGDNLSYIAKKYKTTVKQIQNWNGIKDANKIYAGQKIRVK (nucleotide sequence of wild-type bacteriophage endolyin PlyP825)
SEQ ID NO: 3

```
ATGGCGTTAACAGAAGCATGGCTTCTTGAAAAAGCCAATAGACGTTTAAA

CGAAAAAGGGATGCTTAAAGAAGTTTCAGATAAAACCCGTGCAGTAATTA

AAGAGATGGCTAAACAAGGTATTTACATCAATGTTGCACAAGGCTTCCGT

TCTATTGCAGAACAGAATGAATTATATGCACAAGGCAGAACAAAGCCCGG

CAATGTGGTAACAAATGCAAAGGGAGGTCAATCAAATCATAACTACGGTG

TTGCTGTAGACTTATGCCAATACACGCAAGATGGTAAAGATGTAATCTGG

GCGGTAGATGCTAAGTTTAAAAAGATTGTAGCTGCCATGAAGAAACAAGG

ATTCAAATGGGGTGGAGATTGGAAATCTTTTAAAGACAACCCTCATTTTG

AGTTATATGATTGGGTAGGAGGAGAACGTCCTAACTCCAGCACTCCCGCT

AAACCATCCAAACCATCTACACCTGCGAAGCCTTCTGGTGAACTTGGTCT

CGTAGATTACATGAACAGCAAGAAAATGGATTCCTCTTTTGCTAATCGTA

AAGTACTTGCTGGAAAATATGGCATCAAGAATTATACAGGAACCACTTCA

CAGAATACACAACTATTAGCTAAGATTAAAGCAGGTGCACCAAAACACGC

TACTCCAAAACCTCCGGCTAAACCAGCTACTTCTGGGATGTACGTATACT

TCCCTGCTGGTAAAGGTACTTGGAGTGTGTATCCATTAAATAAAGCACCT
```

-continued

```
GTAAAAGCTAATGCAATCGGAGCAATTAACCCTTCGAAGTTTGGTGGACT

GACTTACAAAGTCGAAAAGAATTACGGAGATAATGTTCTAGGAATTAAGA

CTGGTTCCTTTGGACATGTCAAAGTATATTGCCACCCATCAACTGGTGTA

AAAATTAGCAACAACGGAGCAGGAAATTTTCCGAATGTTCAGAATTAA
```

(polypeptide sequence of bacteriophage endolyin PlyP825; underlined is the EAD of the endolysin)
SEQ ID NO: 4

<u>MALTEAWLLEKANRRLNEKGMLKEVSDKTRAVIKEMAKQGIYINVAQGFR</u>
<u>SIAEQNELYAQGRTKPGNVVTNAKGGQSNHNYGVAVDLCQYTQDGKDVIW</u>
<u>AVDAKFKKIVAAMKKQGFKWGGDWKSFKDNPHFELYDWVGGERPNSSTPA</u>
KPSKPSTPAKPSGELGLVDYMNSKKMDSSFANRKVLAGKYGIKNYTGTTS
QNTQLLAKIKAGAPKHATPKPPAKPATSGMYVYFPAGKGTWSVYPLNKAP
VKANAIGAINPSKFGGLTYKVEKNYGDNVLGIKTGSFGHVKVYCHPSTGV
KISNNGAGNFPNVQN (nucleotide sequence of wild-type bacteriophage endolyin PlyP511)
SEQ ID NO: 5

```
ATGGTAAAATATACCGTAGAGAACAAAATTATTGCAGGATTACCTAAAGG

TAAACTAAAGGGGCTAACTTTGTTATTGCTCATGAAACTGCAAATAGCA

AGTCTACTATTGACAATGAAGTAAGCTACATGACTAGGAACTGGAAGAAC

GCATTTGTAACTCACTTTGTAGGTGGCGGAGGTAGAGTCGTTCAGGTTGC

TAATGTAAACTATGTTTCTTGGGGAGCAGGTCAGTATGCTAACTCTTATT

CCTATGCGCAGGTAGAGTTGTGCCGTACAAGTAATGCAACTACATTTAAG

AAAGACTATGAAGTGTACTGTCAATTACTAGTAGACCTAGCTAAAAAAGC

AGGTATCCCTATTACACTTGACTCTGGTAGTAAAACTAGTGATAAAGGTA

TTAAATCCCATAAATGGGTTGCTGATAAGCTAGGAGGAACAACACACCAA

GACCCATACGCTTACTTAAGCTCATGGGGTATTAGTAAAGCACAATTTGC

TAGTGACTTGGCTAAAGTATCTGGCGGAGGAAACACAGGAACAGCGCCAG

CTAAACCAAGCACACCAGCACCTAAACCAAGCACACCATCTACTAACCTA

GACAAACTTGGCTTAGTAGACTACATGAACGCTAAGAAAATGGACTCTAG

CTACAGTAACAGAGATAAGTTAGCTAAACAGTATGGTATTGCTAACTATT

CAGGAACAGCTAGCCAGAACACTACACTCCTTAGTAAAATTAAAGGAGGA

GCACCTAAACCAAGCACACCAGCACCTAAACCTAGTACATCTACAGCTAA

GAAAATTTATTTCCCACCAAATAAAGGAAACTGGTCTGTGTATCCAACAA

ATAAAGCACCCGTTAAGGCTAATGCTATTGGTGCTATTAACCCTACTAAA

TTCGGAGGATTGACTTACACTATCCAAAAAGATAGAGGAAACGGTGTATA

CGAAATCCAAACAGACCAATTCGGCAGAGTTCAAGTCTATGGTGCACCTA

GTACAGGAGCAGTTATCAAAAAATAA
```

(polypeptide sequence of bacteriophage endolyin PlyP511; underlined is the EAD of the endolysin)
SEQ ID NO: 6

<u>MVKYTVENKIIAGLPKGKLKGANFVIAHETANSKSTIDNEVSYMTRNWKN</u>
<u>AFVTHFVGGGGRVVQVANVNYVSWGAGQYANSYSYAQVELCRTSNATTFK</u>
<u>KDYEVYCQLLVDLAKKAGIPITLDSGSKTSDKGIKSHKWVADKLGGTTHQ</u>
<u>DPYAYLSSWGISKAQFASDLAKVSGGG</u>NTGTAPAKPSTPAPKPSTPSTNL

-continued

DKLGLVDYMNAKKMDSSYSNRDKLAKQYGIANYSGTASQNTTLLSKIKGG

APKPSTPAPKPSTSTAKKIYFPPNKGNWSVYPTNKAPVKANAIGAINPTK

FGGLTYTIQKDRGNGVYEIQTDQFGRVQVYGAPSTGAVIKK (nucleotide sequence of codon optimized
bacteriophage endolyin PlyP40; optimized for E.
coli sequence identity with wild-type PlyP40 is
74%)
SEQ ID NO: 7
ATGGCATTAGTCCTCGACATCAGCAAGTGGCAACCGACGGTAAACTATAG

CGGTCTGAAAGAGGATGTGGGTTTTGTGGTCATCCGTAGCTCCAATGGTA

CGCAGAAATATGACGAACGCCTGGAACAGCACGCGAAAGGTCTGGACAAA

GTTGGTATGCCGTTTGGTCTGTACCATTACGCGCTGTTTGAGGGTGGTCA

AGACACCATTAATGAAGCAAACATGTTGGTTAGCGCGTACAAGAAATGCC

GTCAGCTGGGTGCCGAGCCGACTTTCCTGTTCCTGGATTACGAAGAAGTG

AAGCTGAAGTCCGGCAACGTCGTGAATGAGTGTCAGCGCTTCATTGACCA

CGTTAAAGGTCAAACGGGTGTCAAAGTTGGCTTGTATGCGGGCGATAGCT

TCTGGAAAACCCACGACCTGGATAAGGTCAAGCATGACTTGCGCTGGGTC

GCGCGTTACGGCGTGGATAACGGTAAGCCGAGCACCAAACCGAGCATCCC

GTACGACCTGTGGCAGTATACTTCCAAAGGCCGTATTAAGGCCATTGCTA

GCCCGGTCGATATGAACACCTGCAGCAGCGACATCCTGAACAAGCTGAAA

GGTAGCAAAGCGCCGGTGAAACCTGCGCCGAAGCCGACCCCGAGCAAGCC

AGCACCAGCGAAACCGGCTCCTAAAACGACCACCAAATATGTTAATACCG

CGCACCTGAACATCCGTGAGAAGGCAAGCGCCGACTCCAAGGTTCTGGGC

GTGCTGGATCTGAACGACAGCGTTCAAGTTATTAGCGAGAGCGGTGGCTG

GTCTAAGCTGAAAAGCGGCAACAAGCAAGTTTACGTCAGCAGCAAGTATC

TGAGCAAATCGAAAACGACCCCGAAAGCAAAGCCGAGCTCGAAGCAATAC

TATACCATTAAGTCTGGCGATAATCTGTCTTACATTGCCAAAAAGTACAA

GACCACGGTGAAACAGATCCAGAATTGGAATGGTATCAAGGATGCTAATA

AGATCTATGCGGGCCAGAAAATTCGTGTGAAATAA (nucleotide sequence of codon optimized
bacteriophage endolyin PlyP825; optimized for E.
coli; sequence identity with wild-type PlyP825 is
77%)
SEQ ID NO: 8
ATGGCACTGACGGAAGCCTGGCTGCTCGAAAAAGCGAACAGAAGATTGAA

CGAAAAGGGCATGCTGAAAGAAGTTAGCGACAAGACGCGTGCTGTGATCA

AAGAGATGGCGAAACAGGGTATTTACATTAACGTTGCGCAAGGTTTCCGC

AGCATTGCGGAGCAGAATGAGCTGTATGCCCAGGGCCGCACCAAGCCGGG

TAACGTCGTTACCAATGCGAAAGGTGGTCAATCCAACCACAATTATGGCG

TCGCTGTGGACTTGTGCCAATATACTCAGGATGGCAAAGACGTGATCTGG

GCGGTTGATGCGAAGTTTAAGAAGATCGTTGCCGCGATGAAGAAACAAGG

TTTCAAATGGGGTGGTGACTGGAAGTCCTTTAAAGACAATCCGCACTTCG

AGCTGTACGATTGGGTGGGCGGTGAACGTCCGAACAGCTCCACCCCGGCT

AAACCGAGCAAACCAAGCACGCCGGCAAAACCGTCTGGTGAGCTGGGCCT

GGTTGATTACATGAACAGCAAAAAGATGGACAGCTCTTTCGCAAATCGTA

AAGTTCTGGCGGGCAAATATGGTATCAAGAACTATACTGGCACCACCTCG

CAGAATACGCAACTGCTGGCCAAGATTAAAGCAGGTGCACCGAAACATGC

CACCCCGAAACCTCCGGCAAAGCCAGCGACCAGCGGTATGTACGTGTACT

TTCCGGCAGGTAAGGGCACGTGGAGCGTGTATCCGCTGAATAAGGCGCCT

GTGAAAGCGAACGCTATTGGTGCGATCAACCCGAGCAAGTTCGGTGGTCT

GACCTACAAGGTCGAGAAGAACTACGGCGATAACGTGCTGGGTATCAAAA

CGGGCAGCTTTGGCCACGTCAAGGTTTACTGTCATCCGAGCACCGGTGTC

AAGATTAGCAATAATGGTGCCGGCAATTTCCCGAACGTCCAGAATTAA (nucleotide sequence of codon optimized
bacteriophage endolyin PlyP511; optimized for E.
coli; sequence identity with wild-type PlyP511 is
75%)
SEQ ID NO: 9
ATGGTCAAATACACCGTCGAGAACAAAATCATCGCAGGCTTACCTAAGGG

CAAATTGAAGGGCGCAAACTTTGTTATTGCCCATGAGACTGCGAATAGCA

AAAGCACGATTGATAACGAGGTTTCTTATATGACCCGTAACTGGAAGAACG

CCTTCGTCACGCACTTTGTGGGTGGTGGTGGCCGTGTCGTTCAGGTGGCG

AATGTGAACTATGTTAGCTGGGGTGCGGGTCAGTACGCCAATTCCTACAG

CTACGCGCAGGTCGAACTGTGTCGTACGAGCAACGCCACGACGTTTAAGA

AGGACTATGAAGTATACTGCCAATTGCTGGTGGATCTGGCGAAGAAAGCG

GGCATCCCGATTACGCTGGATAGCGGTAGCAAAACCAGCGACAAAGGTAT

TAAGTCGCACAAGTGGGTGGCGGATAAACTGGGTGGTACTACCCATCAGG

ACCCGTACGCATACCTGAGCAGCTGGGGCATCAGCAAGGCGCAATTCGCA

TCCGACTTGGCGAAAGTTAGCGGCGGTGGCAATACCGGCACGGCTCCGGC

TAAACCGAGCACTCCAGCCCCTAAGCCAAGCACCCCGTCTACCAACCTGG

ACAAGCTGGGCCTGGTGGATTACATGAATGCGAAGAAAATGGACAGCTCG

TACAGCAATCGCGATAAGCTGGCAAAACAGTACGGTATCGCGAACTATTC

CGGCACCGCTAGCCAGAATACCACCCTGCTGAGCAAGATCAAGGGTGGTG

CTCCGAAGCCGAGCACCCCGGCACCGAAACCGTCTACGAGCACCGCGAAA

AAGATTTACTTTCCGCCGAATAAAGGTAACTGGAGCGTTTATCCGACGAA

CAAAGCGCCGGTCAAAGCGAATGCAATTGGTGCAATTAACCCGACCAAGT

TCGGTGGCCTGACCTATACCATTCAAAAAGACCGTGGCAATGGTGTTTAT

GAAATCCAGACCGACCAATTCGGTCGCGTTCAAGTCTATGGTGCGCCGTC

CACGGGTGCCGTGATCAAGAAATAA

EXAMPLES

Example 1

Treatment of Mozzarella with an endolysin and pediocin

In the following experiment, the antimicrobial effect on growth of *Listeria monocytogenes* on Mozzarella cheese is shown after treatment with endolysin P40 and pediocin.

A frozen vial with the strain *Listeria monocytogenes* LSH377 was thawed and added to 30 ml PCB medium (5 g/l bacto tripton; 2.5 g/l bacto yeast extract; 1 g/l dextrose; 15 g/l bacto agar; pH 7) in a sterile Erlenmeyer flask. Pre-cultivation at 37° C. was done during 21 hours. Subsequently the culture was diluted in a sterile MES buffer (5 mM MES hydrate [2-(N-morpholino)ethanesulfonic acid]+50 mM NaCl, pH 6.0) to a final solution of approximately 4×10⁶ cell/ml. The diluted strain was directly plated on *Listeria* selective plates (Oxford plates) for the determination of the final inoculated amount.

A pediocin from *Pediococcus acidilactici* (Sigma-Aldrich; product number P0098) stock solution was made comprising 0.1 mg/ml pediocin in 0.1 M sodium acetate pH 5.0.

Slices of Mozzarella cheese were prepared with a size of 2 cm×5 cm×1 cm and a surface area of 2 cm×5 cm was used. The pieces of Mozzarella cheese were placed in petri dishes for further treatment.

Tests were done in duplo. 50 µl of the diluted *Listeria* inoculum was brought on to the top surface of the Mozzarella pieces. The inoculum was distributed evenly over the 10 cm² surface with a metal spreader. The pieces were dried in open air for 8 minutes.

After drying, the Mozzarella pieces were treated with the following compositions.
1) Composition A (control): 50 µl of MES (5 mM MES hydrate [2-(N-morpholino)ethanesulfonic acid]+50 mM NaCl, pH 6.0),
2) Composition B: 50 µl of MES (5 mM MES hydrate [2-(N-morpholino)ethanesulfonic acid]+50 mM NaCl, pH 6.0) containing 400 µg/ml bacteriophage endolysin plyP40,
3) Composition C: 50 µl of MES (5 mM MES hydrate [2-(N-morpholino)ethanesulfonic acid]+50 mM NaCl, pH 6.0) containing 50 µg/ml pediocin,
4) Composition D: 50 µl of MES (5 mM MES hydrate [2-(N-morpholino)ethanesulfonic acid]+50 mM NaCl, pH 6.0) containing 400 µg/ml bacteriophage endolysin plyP40+50 µg/ml pediocin.

The respective compositions were brought onto the inoculated surface of the Mozzarella pieces and distributed evenly with a metal spreader. The pieces were dried in open air for 1 hour. After drying, the samples were individually packed in sterile plastic bags (volume 80 ml). The 1 hour samples were plated out directly, the remaining samples were incubated at 15° C. for 24 and 72 hours.

At each time point, 2 samples of each treatment were used for determination of viable counts.

In the plastic bag 20 ml sterile MES buffer was added to Mozzarella pieces. The cheese was shaken and rubbed for approximately 30 seconds to allow *Listeria* cells to detach from the cheese. Additional serial dilutions were made in sterile physiological saline. 100 µl of the liquid sample material was pipetted onto a *Listeria* selective plate (Modified Oxford medium agar; MOX) and distributed evenly by using a metal spreader. The *Listeria* selective plates were incubated at 37° C. for 48 hours. After incubation, the *Listeria monocytogenes* colonies were counted and calculated back to the amount of *Listeria* present on the cheese surface.

The results are shown in Table 1. They clearly demonstrate that the composition comprising bacteriophage endolysin PlyP40 and pediocin protects Mozzarella better against *Listeria* than endolysin or pediocin alone.

The synergy of both active ingredients was calculated according to the Colby equation (Colby, 1967):

$$E = X + Y - [(X \cdot Y)/100]$$

wherein X and Y are the observed antibacterial activities (in %) of the individual active ingredients X and Y, respectively. If the observed antibacterial activity (O in %) of the combination exceeds the expected antibacterial activity (E in %) of the combination and the synergy factor O/E is thus >1.0, the combined application of the active ingredients leads to a synergistic antifungal effect. The synergy factor of the combination of the bacteriophage endolysin and pediocin resulted in a synergy factor of 1.15.

Surprisingly, the combined application of bacteriophage endolysin PlyP40 and pediocin leads to a strong synergistic reduction in infection.

Example 2

Treatment of Mozzarella with an endolysin and nisin

In the following experiment, the antimicrobial effect on growth of *Listeria monocytogenes* on Mozzarella cheese is shown after treatment with endolysin P40 and nisin. The experiment is done essentially as described in Example 1.

The results clearly demonstrate that the composition comprising bacteriophage endolysin PlyP40 and nisin protects Mozzarella better against *Listeria* than endolysin or nisin alone.

Example 3

Treatment of Mozzarella with an Endolysin and Levulinic Acid

In the following experiment, the antimicrobial effect on growth of *Listeria monocytogenes* on Mozzarella cheese is shown after treatment with endolysin P40 and levulinic acid. The experiment is done essentially as described in Example 1.

The results clearly demonstrate that the composition comprising bacteriophage endolysin PlyP40 and levulinic acid protects Mozzarella better against *Listeria* than endolysin or levulinic acid alone.

Example 4

Treatment of Mozzarella with an endolysin and propionic acid

In the following experiment, the antimicrobial effect on growth of *Listeria monocytogenes* on Mozzarella cheese is shown after treatment with endolysin P40 and propionic acid. The experiment is done essentially as described in Example 1.

The results clearly demonstrate that the composition comprising bacteriophage endolysin PlyP40 and propionic acid protects Mozzarella better against *Listeria* than endolysin or propionic acid alone.

Example 5

Treatment of Mozzarella with an endolysin and acetic acid

In the following experiment, the antimicrobial effect on growth of *Listeria monocytogenes* on Mozzarella cheese is shown after treatment with endolysin P40 and acetic acid. The experiment is done essentially as described in Example 1.

The results clearly demonstrate that the composition comprising bacteriophage endolysin PlyP40 and acetic acid protects Mozzarella better against *Listeria* than endolysin or acetic acid alone.

Example 6

Treatment of Mozzarella with an endolysin and lauric arginate

In the following experiment, the antimicrobial effect on growth of *Listeria monocytogenes* on Mozzarella cheese is shown after treatment with endolysin P40 and lauric arginate. The experiment is done essentially as described in Example 1.

The results clearly demonstrate that the composition comprising bacteriophage endolysin PlyP40 and lauric arginate protects Mozzarella better against *Listeria* than endolysin or lauric arginate alone.

Example 7

Treatment of Mozzarella with an endolysin and a lactoperoxidase system

In the following experiment, the antimicrobial effect on growth of *Listeria monocytogenes* on Mozzarella cheese is shown after treatment with endolysin P40 and a lactoperoxidase system. The experiment is done essentially as described in Example 1.

The results clearly demonstrate that the composition comprising bacteriophage endolysin PlyP40 and a lactoperoxidase system protects Mozzarella better against *Listeria* than endolysin or a lactoperoxidase system alone.

Example 8

Treatment of Mozzarella with an endolysin and a phage

In the following experiment, the antimicrobial effect on growth of *Listeria monocytogenes* on Mozzarella cheese is shown after treatment with endolysin P40 and a phage. The experiment is done essentially as described in Example 1. The phage used in Listex™ P100 phage.

The results clearly demonstrate that the composition comprising bacteriophage endolysin PlyP40 and a phage protects Mozzarella better against *Listeria* than endolysin or a phage alone.

Example 9

Treatment of Mozzarella with an endolysin and a sophorolipid

In the following experiment, the antimicrobial effect on growth of *Listeria monocytogenes* on Mozzarella cheese is shown after treatment with endolysin P40 and a sophorolipid. The experiment is done essentially as described in Example 1.

The results clearly demonstrate that the composition comprising bacteriophage endolysin PlyP40 and a sophorolipid protects Mozzarella better against *Listeria* than endolysin or the sophorolipid alone.

TABLE 1

Amount of *Listeria* after treatment of Mozzarella with various antimicrobial compositions.

| Composition | Amount of *Listeria* after 1 hour (in %)* | Amount of *Listeria* after 24 hours (in %)* | Amount of *Listeria* after 72 hours (in %)* |
| --- | --- | --- | --- |
| Composition A | 100 | 100 | 100 |
| Composition B | 34 | 24 | 20 |
| Composition C | 48 | 25 | 21 |
| Composition D | 3 | 6 | 3 |

*Amount in %; control was set at 100%

REFERENCES

Celia L K, Nelson D and Kerr D E (2007), Characterization of a bacteriophage lysin (Ply700) from *Streptococcus uberis*. Vet. Microbiol. 130:107-117.

Colby S R (1967), Calculating synergistic and antagonistic responses of herbicide combination. Weeds 15: 20-22.

Mayer M J, Narbad A, and Gasson M J (2008), Molecular characterization of a *Clostridium difficile* bacteriophage and its cloned biologically active endolysin. J. Bacteriol. 190:6734-6740.

Obeso J M, Martinez B, Rodriguez A, and Garcia P (2008), Lytic activity of the recombinant staphylococcal bacteriophage phiH5 endolysin active against *Staphylococcus aureus* in milk. Int. J. Food Microbiol. 128: 212-218.

The invention claimed is:

1. A composition comprising a bacteriophage endolysin and pediocin, wherein the bacteriophage endolysin is a polypeptide selected from the group consisting of:
   (a) a polypeptide comprising an amino acid sequence as set out in SEQ ID NO:2, 4 or 6;
   (b) a polypeptide comprising an amino acid sequence having at least 90% sequence identity with the amino acid sequence of SEQ ID NO:2, 4 or 6;
   (c) a polypeptide comprising an amino acid sequence having at least 90% sequence identity with the enzymatically active domain of the amino acid sequence of SEQ ID NO:2, 4 or 6;
   (d) a polypeptide encoded by a polynucleotide comprising the polynucleotide sequence as set out in SEQ ID NO:1, 3 or 5;
   (e) a polypeptide encoded by a polynucleotide comprising a polynucleotide sequence having at least 90% sequence identity with the enzymatically active domain coding sequence in SEQ ID NO:1, 3 or 5;
   (f) a polypeptide encoded by a polynucleotide which hybridizes with the complementary strand of SEQ ID NO:1, 3 or 5;
   (g) a polypeptide encoded by a polynucleotide which hybridizes with the complementary strand of a polynucleotide having at least 90% sequence identity with the enzymatically active domain coding sequence in SEQ ID NO:1, 3 or 5; and
   (h) a fragment at least 148 amino acids in length of a polypeptide as defined in (a), (b), (c), (d), (e), (f), or (g).

2. A composition according to claim 1, wherein the bacteriophage endolysin is capable of specifically lysing bacteria of the genus *Listeria*.

3. A composition according to claim 1, wherein the amount of the bacteriophage endolysin is in a range from 0.1 µg/ml to 1000 µg/ml.

4. A composition according to claim 1, wherein the amount of pediocin is in a range from 0.001 µg/ml to 1000 µg/ml.

5. A kit comprising a bacteriophage endolysin and pediocin, wherein the bacteriophage endolysin is a polypeptide selected from the group consisting of:
   (a) a polypeptide comprising an amino acid sequence as set out in SEQ ID NO:2, 4 or 6:
   (b) a polypeptide comprising an amino acid sequence having at least 90% sequence identity with the amino acid sequence of SEQ ID NO:2, 4 or 6;
   (c) a polypeptide comprising an amino acid sequence having at least 90% sequence identity with the enzymatically active domain of the amino acid sequence of SEQ ID NO:2, 4 or 6:
   (d) a polypeptide encoded by a polynucleotide comprising the polynucleotide sequence as set out in SEQ ID NO:1, 3 or 5:
   (e) a polypeptide, encoded by a polynucleotide comprising a polynucleotide sequence having at least 90% sequence identity with the enzymatically active domain coding sequence in SEQ ID NO:1, 3 or 5;
   (f) a polypeptide encoded by a polynucleotide which hybridizes with the complementary strand of SEQ ID NO:1, 3 or 5:
   (g) a polypeptide encoded by a polynucleotide which hybridizes with the complementary strand of a polynucleotide having at least 90% sequence identity with the enzymatically active domain coding sequence in SEQ ID NO:1, 3 or 5; and
   (h) a fragment at least 148 amino acids in length of a polypeptide as defined in (a), (b), (c), (d), (e), (f), or (g).

6. A product comprising a bacteriophage endolysin and pediocin, wherein the bacteriophage endolysin is a polypeptide selected from the group consisting of:
   (a) a polypeptide comprising an amino acid sequence as set out in SEQ ID NO:2, 4 or 6:
   (b) a polypeptide comprising an amino acid sequence having at least 90% sequence identity with the amino acid sequence of SEQ ID NO:2, 4 or 6;
   (c) a polypeptide comprising an amino acid sequence having at least 90% sequence identity with the enzymatically active domain of the amino acid sequence of SEQ ID NO:2, 4 or 6:
   (d) a polypeptide encoded by a polynucleotide comprising the polynucleotide sequence as set out in SEQ NO:1, 3 or 5:
   (e) a polypeptide encoded by a polynucleotide comprising a polynucleotide sequence having at least 90% sequence identity with the enzymatically active domain coding sequence in SEQ ID NO:1, 3 or 5;
   (f) a polypeptide encoded by a polynucleotide which hybridizes with the complementary strand of SEQ ID NO:1, 3 or 5:
   (g) a polypeptide encoded by a polynucleotide which hybridizes with the complementary strand of a polynucleotide having at least 90% sequence identity with the enzymatically active domain coding sequence in SEQ ID NO:1, 3 or 5; and
   (h) a fragment at least 148 amino acids in length of a polypeptide as defined in (a), (b), (c), (d), (e), (f), or (g).

7. A product according to claim 6, wherein the product is selected from the group consisting of a food product, a feed product, a pharmaceutical product, a cosmetic product and an agricultural product.

8. A product according to claim 7, wherein the food product is selected from the group consisting of dairy products, meat products, fish products, beverage products, baking products, unpasteurized food products, salads, and sauces, marinades, salsas and seasonings.

9. A composition according to claim 1, wherein the bacteriophage endolysin is a polypeptide selected from the group consisting of:
   (a) a polypeptide comprising an amino acid sequence having at least 90% sequence identity with amino acids 1 to 202 of SEQ ID NO: 2;
   (b) a polypeptide comprising an amino acid sequence having at least 90% sequence identity with amino acids 1 to 148 of SEQ ID NO: 4;
   (c) a polypeptide comprising an amino acid sequence having at least 90% sequence identity with amino acids 1 to 182 of SEQ ID NO: 6;
   (d) a polypeptide encoded by a polynucleotide comprising a polynucleotide sequence having at least 90% sequence identity with the nucleotides 1 to 606 of SEQ ID NO: 1;
   (e) a polypeptide encoded by a polynucleotide comprising a polynucleotide sequence having at least 90% sequence identity with the nucleotides 1 to 444 of SEQ ID NO: 3; and
   (f) a polypeptide encoded by a polynucleotide comprising a polynucleotide sequence having at least 90% sequence identity with the nucleotides 1 to 546 of SEQ ID NO: 5.

* * * * *

SEQUENCE LISTING

```
<160> NUMBER OF SEQ ID NOS: 9

<210> SEQ ID NO 1
<211> LENGTH: 1035
<212> TYPE: DNA
<213> ORGANISM: Unknown
<220> FEATURE:
<223> OTHER INFORMATION: Nucleotide sequence of wild-type bacteriophage
      endolyin PlyP40
<220> FEATURE:
<221> NAME/KEY: CDS
<222> LOCATION: (1)..(1035)
<223> OTHER INFORMATION: /transl_table=1

<400> SEQUENCE: 1 atg gcg tta gtt tta gac att tca aaa tgg caa ccg aca gtg aat tat    48
Met Ala Leu Val Leu Asp Ile Ser Lys Trp Gln Pro Thr Val Asn Tyr
1               5                   10                  15 tca gga cta aaa gaa gat gta gga ttc gtt gtc att cgt tct agc aac    96
Ser Gly Leu Lys Glu Asp Val Gly Phe Val Val Ile Arg Ser Ser Asn
            20                  25                  30 gga aca cag aag tat gat gag aga tta gag caa cac gca aaa ggc tta   144
Gly Thr Gln Lys Tyr Asp Glu Arg Leu Glu Gln His Ala Lys Gly Leu
        35                  40                  45 gat aaa gtg gga atg cct ttc gga ctg tac cac tac gct tta ttt gaa   192
```

```
                Asp Lys Val Gly Met Pro Phe Gly Leu Tyr His Tyr Ala Leu Phe Glu
                     50                  55                  60 ggt gga caa gat act atc aat gaa gcg aat atg tta gtt agc gca tat          240
Gly Gly Gln Asp Thr Ile Asn Glu Ala Asn Met Leu Val Ser Ala Tyr
 65                  70                  75                  80 aag aaa tgt cgt caa tta ggc gca gaa cca aca ttc ttg ttc tta gat          288
Lys Lys Cys Arg Gln Leu Gly Ala Glu Pro Thr Phe Leu Phe Leu Asp
                 85                  90                  95 tat gaa gaa gtc aag tta aaa tct ggt aat gtg gta aac gaa tgt cag          336
Tyr Glu Glu Val Lys Leu Lys Ser Gly Asn Val Val Asn Glu Cys Gln
             100                 105                 110 aga ttt ata gac cat gtg aaa ggt caa act ggg gtc aaa gta gga ctt          384
Arg Phe Ile Asp His Val Lys Gly Gln Thr Gly Val Lys Val Gly Leu
             115                 120                 125 tat gct ggg gat agt ttt tgg aag acg cac gat tta gat aaa gtc aag          432
Tyr Ala Gly Asp Ser Phe Trp Lys Thr His Asp Leu Asp Lys Val Lys
    130                 135                 140 cac gat tta aga tgg gta gct aga tat ggg gta gat aac ggt aaa ccg          480
His Asp Leu Arg Trp Val Ala Arg Tyr Gly Val Asp Asn Gly Lys Pro
145                 150                 155                 160 tct aca aaa cca tct ata cct tat gat ttg tgg cag tat act tcc aag          528
Ser Thr Lys Pro Ser Ile Pro Tyr Asp Leu Trp Gln Tyr Thr Ser Lys
                165                 170                 175 ggg cga att aaa gcc att gct tca cct gta gat atg aat aca tgt tct          576
Gly Arg Ile Lys Ala Ile Ala Ser Pro Val Asp Met Asn Thr Cys Ser
            180                 185                 190 agc gac ata ttg aac aaa tta aaa ggt tca aaa gca cct gtt aaa cca          624
Ser Asp Ile Leu Asn Lys Leu Lys Gly Ser Lys Ala Pro Val Lys Pro
            195                 200                 205 gca cca aaa ccg aca cct agt aag cca gca cca gcg aaa cca gca cca          672
Ala Pro Lys Pro Thr Pro Ser Lys Pro Ala Pro Ala Lys Pro Ala Pro
    210                 215                 220 aaa acg act act aaa tat gtc aat acg gca cat tta aat att cgt gaa          720
Lys Thr Thr Thr Lys Tyr Val Asn Thr Ala His Leu Asn Ile Arg Glu
225                 230                 235                 240 aag gca agt gct gac tcg aaa gta ttg gga gtt ctt gac ctc aac gat          768
Lys Ala Ser Ala Asp Ser Lys Val Leu Gly Val Leu Asp Leu Asn Asp
                245                 250                 255 tcc gta cag gtc att tct gaa tca ggt gga tgg tct aag ttg aaa tct          816
Ser Val Gln Val Ile Ser Glu Ser Gly Gly Trp Ser Lys Leu Lys Ser
            260                 265                 270 ggg aac aag caa gta tat gtt tct agc aag tat ctt agt aag tca aaa          864
Gly Asn Lys Gln Val Tyr Val Ser Ser Lys Tyr Leu Ser Lys Ser Lys
            275                 280                 285 acg aca ccg aag gcg aaa cca agc tcg aaa cag tat tat act att aaa          912
Thr Thr Pro Lys Ala Lys Pro Ser Ser Lys Gln Tyr Tyr Thr Ile Lys
    290                 295                 300 agc ggt gat aat tta agt tac att gct aag aag tat aaa act aca gta          960
Ser Gly Asp Asn Leu Ser Tyr Ile Ala Lys Lys Tyr Lys Thr Thr Val
305                 310                 315                 320 aaa cag att caa aac tgg aac ggt atc aag gat gct aac aaa att tac         1008
Lys Gln Ile Gln Asn Trp Asn Gly Ile Lys Asp Ala Asn Lys Ile Tyr
                325                 330                 335 gca ggt caa aaa att aga gtt aaa taa                                      1035
Ala Gly Gln Lys Ile Arg Val Lys
            340

<210> SEQ ID NO 2
<211> LENGTH: 344
<212> TYPE: PRT
```

<213> ORGANISM: Unknown
<220> FEATURE:
<223> OTHER INFORMATION: Synthetic Construct

<400> SEQUENCE: 2

Met Ala Leu Val Leu Asp Ile Ser Lys Trp Gln Pro Thr Val Asn Tyr
1               5                   10                  15

Ser Gly Leu Lys Glu Asp Val Gly Phe Val Ile Arg Ser Ser Asn
            20                  25                  30

Gly Thr Gln Lys Tyr Asp Glu Arg Leu Glu Gln His Ala Lys Gly Leu
            35                  40                  45

Asp Lys Val Gly Met Pro Phe Gly Leu Tyr His Tyr Ala Leu Phe Glu
50                  55                  60

Gly Gly Gln Asp Thr Ile Asn Glu Ala Asn Met Leu Val Ser Ala Tyr
65                  70                  75                  80

Lys Lys Cys Arg Gln Leu Gly Ala Glu Pro Thr Phe Leu Phe Leu Asp
                85                  90                  95

Tyr Glu Glu Val Lys Leu Lys Ser Gly Asn Val Val Asn Glu Cys Gln
                100                 105                 110

Arg Phe Ile Asp His Val Lys Gly Gln Thr Gly Val Lys Val Gly Leu
                115                 120                 125

Tyr Ala Gly Asp Ser Phe Trp Lys Thr His Asp Leu Asp Lys Val Lys
130                 135                 140

His Asp Leu Arg Trp Val Ala Arg Tyr Gly Val Asp Asn Gly Lys Pro
145                 150                 155                 160

Ser Thr Lys Pro Ser Ile Pro Tyr Asp Leu Trp Gln Tyr Thr Ser Lys
                165                 170                 175

Gly Arg Ile Lys Ala Ile Ala Ser Pro Val Asp Met Asn Thr Cys Ser
                180                 185                 190

Ser Asp Ile Leu Asn Lys Leu Lys Gly Ser Lys Ala Pro Val Lys Pro
                195                 200                 205

Ala Pro Lys Pro Thr Pro Ser Lys Pro Ala Pro Lys Pro Ala Pro
                210                 215                 220

Lys Thr Thr Thr Lys Tyr Val Asn Thr Ala His Leu Asn Ile Arg Glu
225                 230                 235                 240

Lys Ala Ser Ala Asp Ser Lys Val Leu Gly Val Leu Asp Leu Asn Asp
                245                 250                 255

Ser Val Gln Val Ile Ser Glu Ser Gly Gly Trp Ser Lys Leu Lys Ser
                260                 265                 270

Gly Asn Lys Gln Val Tyr Val Ser Ser Lys Tyr Leu Ser Lys Ser Lys
                275                 280                 285

Thr Thr Pro Lys Ala Lys Pro Ser Ser Lys Gln Tyr Tyr Thr Ile Lys
                290                 295                 300

Ser Gly Asp Asn Leu Ser Tyr Ile Ala Lys Lys Tyr Lys Thr Thr Val
305                 310                 315                 320

Lys Gln Ile Gln Asn Trp Asn Gly Ile Lys Asp Ala Asn Lys Ile Tyr
                325                 330                 335

Ala Gly Gln Lys Ile Arg Val Lys
                340

<210> SEQ ID NO 3
<211> LENGTH: 948
<212> TYPE: DNA
<213> ORGANISM: Unknown
<220> FEATURE:
<223> OTHER INFORMATION: Nucleotide sequence of wild-type bacteriophage endolyin PlyP825
<220> FEATURE:
<221> NAME/KEY: CDS
<222> LOCATION: (1)..(948)
<223> OTHER INFORMATION: /transl_table=1

<400> SEQUENCE: 3

```
atg gcg tta aca gaa gca tgg ctt ctt gaa aaa gcc aat aga cgt tta    48
Met Ala Leu Thr Glu Ala Trp Leu Leu Glu Lys Ala Asn Arg Arg Leu
1               5                   10                  15 aac gaa aaa ggg atg ctt aaa gaa gtt tca gat aaa acc cgt gca gta    96
Asn Glu Lys Gly Met Leu Lys Glu Val Ser Asp Lys Thr Arg Ala Val
            20                  25                  30 att aaa gag atg gct aaa caa ggt att tac atc aat gtt gca caa ggc   144
Ile Lys Glu Met Ala Lys Gln Gly Ile Tyr Ile Asn Val Ala Gln Gly
        35                  40                  45 ttc cgt tct att gca gaa cag aat gaa tta tat gca caa ggc aga aca   192
Phe Arg Ser Ile Ala Glu Gln Asn Glu Leu Tyr Ala Gln Gly Arg Thr
    50                  55                  60 aag ccc ggc aat gtg gta aca aat gca aag gga ggt caa tca aat cat   240
Lys Pro Gly Asn Val Val Thr Asn Ala Lys Gly Gly Gln Ser Asn His
65                  70                  75                  80 aac tac ggt gtt gct gta gac tta tgc caa tac acg caa gat ggt aaa   288
Asn Tyr Gly Val Ala Val Asp Leu Cys Gln Tyr Thr Gln Asp Gly Lys
                85                  90                  95 gat gta atc tgg gcg gta gat gct aag ttt aaa aag att gta gct gcc   336
Asp Val Ile Trp Ala Val Asp Ala Lys Phe Lys Lys Ile Val Ala Ala
            100                 105                 110 atg aag aaa caa gga ttc aaa tgg ggt gga gat tgg aaa tct ttt aaa   384
Met Lys Lys Gln Gly Phe Lys Trp Gly Gly Asp Trp Lys Ser Phe Lys
        115                 120                 125 gac aac cct cat ttt gag tta tat gat tgg gta gga gga gaa cgt cct   432
Asp Asn Pro His Phe Glu Leu Tyr Asp Trp Val Gly Gly Glu Arg Pro
    130                 135                 140 aac tcc agc act ccc gct aaa cca tcc aaa cca tct aca cct gcg aag   480
Asn Ser Ser Thr Pro Ala Lys Pro Ser Lys Pro Ser Thr Pro Ala Lys
145                 150                 155                 160 cct tct ggt gaa ctt ggt ctc gta gat tac atg aac agc aag aaa atg   528
Pro Ser Gly Glu Leu Gly Leu Val Asp Tyr Met Asn Ser Lys Lys Met
                165                 170                 175 gat tcc tct ttt gct aat cgt aaa gta ctt gct gga aaa tat ggc atc   576
Asp Ser Ser Phe Ala Asn Arg Lys Val Leu Ala Gly Lys Tyr Gly Ile
            180                 185                 190 aag aat tat aca gga acc act tca cag aat aca caa cta tta gct aag   624
Lys Asn Tyr Thr Gly Thr Thr Ser Gln Asn Thr Gln Leu Leu Ala Lys
        195                 200                 205 att aaa gca ggt gca cca aaa cac gct act cca aaa cct ccg gct aaa   672
Ile Lys Ala Gly Ala Pro Lys His Ala Thr Pro Lys Pro Pro Ala Lys
    210                 215                 220 cca gct act tct ggg atg tac gta tac ttc cct gct ggt aaa ggt act   720
Pro Ala Thr Ser Gly Met Tyr Val Tyr Phe Pro Ala Gly Lys Gly Thr
225                 230                 235                 240 tgg agt gtg tat cca tta aat aaa gca cct gta aaa gct aat gca atc   768
Trp Ser Val Tyr Pro Leu Asn Lys Ala Pro Val Lys Ala Asn Ala Ile
                245                 250                 255 gga gca att aac cct tcg aag ttt ggt gga ctg act tac aaa gtc gaa   816
Gly Ala Ile Asn Pro Ser Lys Phe Gly Gly Leu Thr Tyr Lys Val Glu
            260                 265                 270 aag aat tac gga gat aat gtt cta gga att aag act ggt tcc ttt gga   864
Lys Asn Tyr Gly Asp Asn Val Leu Gly Ile Lys Thr Gly Ser Phe Gly
        275                 280                 285
```

```
cat gtc aaa gta tat tgc cac cca tca act ggt gta aaa att agc aac        912
His Val Lys Val Tyr Cys His Pro Ser Thr Gly Val Lys Ile Ser Asn
    290                 295                 300 aac gga gca gga aat ttt ccg aat gtt cag aat taa                        948
Asn Gly Ala Gly Asn Phe Pro Asn Val Gln Asn
305                 310                 315

<210> SEQ ID NO 4
<211> LENGTH: 315
<212> TYPE: PRT
<213> ORGANISM: Unknown
<220> FEATURE:
<223> OTHER INFORMATION: Synthetic Construct

<400> SEQUENCE: 4
```

Met Ala Leu Thr Glu Ala Trp Leu Leu Glu Lys Ala Asn Arg Arg Leu
1               5                   10                  15

Asn Glu Lys Gly Met Leu Lys Glu Val Ser Asp Lys Thr Arg Ala Val
            20                  25                  30

Ile Lys Glu Met Ala Lys Gln Gly Ile Tyr Ile Asn Val Ala Gln Gly
        35                  40                  45

Phe Arg Ser Ile Ala Glu Gln Asn Glu Leu Tyr Ala Gln Gly Arg Thr
    50                  55                  60

Lys Pro Gly Asn Val Val Thr Asn Ala Lys Gly Gly Gln Ser Asn His
65                  70                  75                  80

Asn Tyr Gly Val Ala Val Asp Leu Cys Gln Tyr Thr Gln Asp Gly Lys
                85                  90                  95

Asp Val Ile Trp Ala Val Asp Ala Lys Phe Lys Lys Ile Val Ala Ala
            100                 105                 110

Met Lys Lys Gln Gly Phe Lys Trp Gly Gly Asp Trp Lys Ser Phe Lys
        115                 120                 125

Asp Asn Pro His Phe Glu Leu Tyr Asp Trp Val Gly Gly Glu Arg Pro
    130                 135                 140

Asn Ser Ser Thr Pro Ala Lys Pro Ser Lys Pro Ser Thr Pro Ala Lys
145                 150                 155                 160

Pro Ser Gly Glu Leu Gly Leu Val Asp Tyr Met Asn Ser Lys Lys Met
                165                 170                 175

Asp Ser Ser Phe Ala Asn Arg Lys Val Leu Ala Gly Lys Tyr Gly Ile
            180                 185                 190

Lys Asn Tyr Thr Gly Thr Thr Ser Gln Asn Thr Gln Leu Leu Ala Lys
        195                 200                 205

Ile Lys Ala Gly Ala Pro Lys His Ala Thr Pro Lys Pro Pro Ala Lys
    210                 215                 220

Pro Ala Thr Ser Gly Met Tyr Val Tyr Phe Pro Ala Gly Lys Gly Thr
225                 230                 235                 240

Trp Ser Val Tyr Pro Leu Asn Lys Ala Pro Val Lys Ala Asn Ala Ile
                245                 250                 255

Gly Ala Ile Asn Pro Ser Lys Phe Gly Gly Leu Thr Tyr Lys Val Glu
            260                 265                 270

Lys Asn Tyr Gly Asp Asn Val Leu Gly Ile Lys Thr Gly Ser Phe Gly
        275                 280                 285

His Val Lys Val Tyr Cys His Pro Ser Thr Gly Val Lys Ile Ser Asn
    290                 295                 300

Asn Gly Ala Gly Asn Phe Pro Asn Val Gln Asn
305                 310                 315

<210> SEQ ID NO 5
<211> LENGTH: 1026
<212> TYPE: DNA
<213> ORGANISM: Unknown
<220> FEATURE:
<223> OTHER INFORMATION: Nucleotide sequence of wild-type bacteriophage
      endolyin PlyP511
<220> FEATURE:
<221> NAME/KEY: CDS
<222> LOCATION: (1)..(1026)
<223> OTHER INFORMATION: /transl_table=1

<400> SEQUENCE: 5

```
atg gta aaa tat acc gta gag aac aaa att att gca gga tta cct aaa      48
Met Val Lys Tyr Thr Val Glu Asn Lys Ile Ile Ala Gly Leu Pro Lys
1               5                   10                  15 ggt aaa cta aaa ggg gct aac ttt gtt att gct cat gaa act gca aat      96
Gly Lys Leu Lys Gly Ala Asn Phe Val Ile Ala His Glu Thr Ala Asn
                20                  25                  30 agc aag tct act att gac aat gaa gta agc tac atg act agg aac tgg     144
Ser Lys Ser Thr Ile Asp Asn Glu Val Ser Tyr Met Thr Arg Asn Trp
            35                  40                  45 aag aac gca ttt gta act cac ttt gta ggt ggc gga ggt aga gtc gtt     192
Lys Asn Ala Phe Val Thr His Phe Val Gly Gly Gly Gly Arg Val Val
        50                  55                  60 cag gtt gct aat gta aac tat gtt tct tgg gga gca ggt cag tat gct     240
Gln Val Ala Asn Val Asn Tyr Val Ser Trp Gly Ala Gly Gln Tyr Ala
65                  70                  75                  80 aac tct tat tcc tat gcg cag gta gag ttg tgc cgt aca agt aat gca     288
Asn Ser Tyr Ser Tyr Ala Gln Val Glu Leu Cys Arg Thr Ser Asn Ala
                85                  90                  95 act aca ttt aag aaa gac tat gaa gtg tac tgt caa tta cta gta gac     336
Thr Thr Phe Lys Lys Asp Tyr Glu Val Tyr Cys Gln Leu Leu Val Asp
                100                 105                 110 cta gct aaa aaa gca ggt atc cct att aca ctt gac tct ggt agt aaa     384
Leu Ala Lys Lys Ala Gly Ile Pro Ile Thr Leu Asp Ser Gly Ser Lys
            115                 120                 125 act agt gat aaa ggt att aaa tcc cat aaa tgg gtt gct gat aag cta     432
Thr Ser Asp Lys Gly Ile Lys Ser His Lys Trp Val Ala Asp Lys Leu
        130                 135                 140 gga gga aca aca cac caa gac cca tac gct tac tta agc tca tgg ggt     480
Gly Gly Thr Thr His Gln Asp Pro Tyr Ala Tyr Leu Ser Ser Trp Gly
145                 150                 155                 160 att agt aaa gca caa ttt gct agt gac ttg gct aaa gta tct ggc gga     528
Ile Ser Lys Ala Gln Phe Ala Ser Asp Leu Ala Lys Val Ser Gly Gly
                165                 170                 175 gga aac aca gga aca gcg cca gct aaa cca agc aca cca gca cct aaa     576
Gly Asn Thr Gly Thr Ala Pro Ala Lys Pro Ser Thr Pro Ala Pro Lys
            180                 185                 190 cca agc aca cca tct act aac cta gac aaa ctt ggc tta gta gac tac     624
Pro Ser Thr Pro Ser Thr Asn Leu Asp Lys Leu Gly Leu Val Asp Tyr
        195                 200                 205 atg aac gct aag aaa atg gac tct agc tac agt aac aga gat aag tta     672
Met Asn Ala Lys Lys Met Asp Ser Ser Tyr Ser Asn Arg Asp Lys Leu
210                 215                 220 gct aaa cag tat ggt att gct aac tat tca gga aca gct agc cag aac     720
Ala Lys Gln Tyr Gly Ile Ala Asn Tyr Ser Gly Thr Ala Ser Gln Asn
225                 230                 235                 240 act aca ctc ctt agt aaa att aaa gga gga gca cct aaa cca agc aca     768
Thr Thr Leu Leu Ser Lys Ile Lys Gly Gly Ala Pro Lys Pro Ser Thr
                245                 250                 255
```

| | | | | | | | | | | | | | | | | |
|---|---|---|---|---|---|---|---|---|---|---|---|---|---|---|---|---|
| cca | gca | cct | aaa | cct | agt | aca | tct | aca | gct | aag | aaa | att | tat | ttc | cca | 816 |
| Pro | Ala | Pro | Lys | Pro | Ser | Thr | Ser | Thr | Ala | Lys | Lys | Ile | Tyr | Phe | Pro | |
| | | 260 | | | | 265 | | | | | 270 | | | | | |
| cca | aat | aaa | gga | aac | tgg | tct | gtg | tat | cca | aca | aat | aaa | gca | ccc | gtt | 864 |
| Pro | Asn | Lys | Gly | Asn | Trp | Ser | Val | Tyr | Pro | Thr | Asn | Lys | Ala | Pro | Val | |
| | | 275 | | | | 280 | | | | 285 | | | | | | |
| aag | gct | aat | gct | att | ggt | gct | att | aac | cct | act | aaa | ttc | gga | gga | ttg | 912 |
| Lys | Ala | Asn | Ala | Ile | Gly | Ala | Ile | Asn | Pro | Thr | Lys | Phe | Gly | Gly | Leu | |
| 290 | | | | | 295 | | | | | 300 | | | | | | |
| act | tac | act | atc | caa | aaa | gat | aga | gga | aac | ggt | gta | tac | gaa | atc | caa | 960 |
| Thr | Tyr | Thr | Ile | Gln | Lys | Asp | Arg | Gly | Asn | Gly | Val | Tyr | Glu | Ile | Gln | |
| 305 | | | | 310 | | | | | 315 | | | | | 320 | | |
| aca | gac | caa | ttc | ggc | aga | gtt | caa | gtc | tat | ggt | gca | cct | agt | aca | gga | 1008 |
| Thr | Asp | Gln | Phe | Gly | Arg | Val | Gln | Val | Tyr | Gly | Ala | Pro | Ser | Thr | Gly | |
| | | | 325 | | | | | 330 | | | | | 335 | | | |
| gca | gtt | atc | aaa | aaa | taa | | | | | | | | | | | 1026 |
| Ala | Val | Ile | Lys | Lys | | | | | | | | | | | | |
| | | 340 | | | | | | | | | | | | | | |

<210> SEQ ID NO 6
<211> LENGTH: 341
<212> TYPE: PRT
<213> ORGANISM: Unknown
<220> FEATURE:
<223> OTHER INFORMATION: Synthetic Construct

<400> SEQUENCE: 6

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
            245                 250                 255

Pro Ala Pro Lys Pro Ser Thr Thr Ala Lys Lys Ile Tyr Phe Pro
        260                 265                 270

Pro Asn Lys Gly Asn Trp Ser Val Tyr Pro Thr Asn Lys Ala Pro Val
    275                 280                 285

Lys Ala Asn Ala Ile Gly Ala Ile Asn Pro Lys Phe Gly Gly Leu
    290                 295                 300

Thr Tyr Thr Ile Gln Lys Asp Arg Gly Asn Val Tyr Glu Ile Gln
305                 310                 315                 320

Thr Asp Gln Phe Gly Arg Val Gln Val Tyr Gly Ala Pro Ser Thr Gly
            325                 330                 335

Ala Val Ile Lys Lys
        340

<210> SEQ ID NO 7
<211> LENGTH: 1035
<212> TYPE: DNA
<213> ORGANISM: Artificial Sequence
<220> FEATURE:
<223> OTHER INFORMATION: Nucleotide sequence of codon optimized
      bacteriophage endolyin PlyP40; optimized for E. coli

<400> SEQUENCE: 7
atggcattag tcctcgacat cagcaagtgg caaccgacgg taaactatag cggtctgaaa        60
gaggatgtgg ttttgtggt catccgtagc tccaatggta cgcagaaata tgacgaacgc       120
ctggaacagc acgcgaaagg tctggacaaa gttggtatgc cgtttggtct gtaccattac       180
gcgctgtttg agggtggtca agacaccatt aatgaagcaa acatgttggt tagcgcgtac       240
aagaaatgcc gtcagctggg tgccgagccg acttttcctgt tcctggatta cgaagaagtg       300
aagctgaagt ccggcaacgt cgtgaatgag tgtcagcgct tcattgacca cgttaaaggt       360 caaacggggtg tcaaagttgg cttgtatgcg ggcgatagct tctggaaaac ccacgacctg       420
gataaggtca gcatgacttt cgctctgggtc gcgcgttacg gcgtggataa cggtaagccg       480
agcaccaaac cgagcatccc cgtacgacctg tggcagtata cttccaaagg ccgtattaag       540
gccattgcta gcccggtcga tatgaacacc tgcagcagcg acatcctgaa caagctgaaa       600
ggtagcaaag cgccggtgaa acctgcgccg aagccgaccc cgagcaagcc agcaccagcg       660
aaaccggctc ctaaaacgac caccaaatat gttaataccg cgcacctgaa catccgtgag       720
aaggcaagcg ccgactccaa ggttctgggc gtgctggatc tgaacgacag cgttcaagtt       780
attagcgaga gcggtggctg gtctaagctg aaaagcggca acaagcaagt ttacgtcagc       840
agcaagtatc tgagcaaatc gaaaacgacc ccgaaagcaa agccgagctc gaagcaatac       900
tataccatta gtctggcga taatctgtct acattgcca aaaagtacaa gaccacggtg       960
aaacagatcc agaattggaa tggtatcaag gatgctaata agatctatgc gggccagaaa      1020
attcgtgtga aataa                                                        1035

<210> SEQ ID NO 8
<211> LENGTH: 948
<212> TYPE: DNA
<213> ORGANISM: Artificial Sequence
<220> FEATURE:
<223> OTHER INFORMATION: Nucleotide sequence of codon optimized
      bacteriophage endolyin PlyP825; optimized for E. coli

<400> SEQUENCE: 8

```
atggcactga cggaagcctg gctgctcgaa aaagcgaaca gaagattgaa cgaaaagggc    60
atgctgaaag aagttagcga caagacgcgt gctgtgatca agagatggc gaaacagggt   120
atttacatta acgttgcgca aggtttccgc agcattgcgg agcagaatga gctgtatgcc   180
cagggccgca ccaagccggg taacgtcgtt accaatgcga aggtggtca atccaaccac   240
aattatggcg tcgctgtgga cttgtgccaa tatactcagg atggcaaaga cgtgatctgg   300
gcggttgatg cgaagtttaa gaagatcgtt gccgcgatga gaaacaagg tttcaaatgg   360
ggtggtgact ggaagtcctt taaagacaat ccgcacttcg agctgtacga ttgggtgggc   420
ggtgaacgtc cgaacagctc cacccccggct aaaccgagca accaagcac gccggcaaaa   480
ccgtctggtg agctgggcct ggttgattac atgaacagca aaaagatgga cagctctttc   540
gcaaatcgta agttctggc gggcaaatat ggtatcaaga actatactgg caccacctcg   600
cagaatacgc aactgctggc caagattaaa gcaggtgcac cgaaacatgc caccccgaaa   660
cctccggcaa agccagcgac cagcggtatg tacgtgtact ttccggcagg taagggcacg   720
tggagcgtgt atccgctgaa taaggcgcct gtgaaagcga acgctattgg tgcgatcaac   780
ccgagcaagt tcggtggtct gacctacaag gtcgagaaga actacggcga taacgtgctg   840
ggtatcaaaa cgggcagctt tggccacgtc aaggtttact gtcatccgag caccggtgtc   900
aagattagca ataatggtgc cggcaatttc ccgaacgtcc agaattaa               948

<210> SEQ ID NO 9
<211> LENGTH: 1026
<212> TYPE: DNA
<213> ORGANISM: Artificial Sequence
<220> FEATURE:
<223> OTHER INFORMATION: Nucleotide sequence of codon optimized
      bacteriophage endolyin PlyP511; optimized for E. coli

<400> SEQUENCE: 9
atggtcaaat acaccgtcga gaacaaaatc atcgcaggct acctaaggg caaattgaag    60
ggcgcaaact ttgttattgc ccatgagact gcgaatagca aaagcacgat tgataacgag   120
gtttcttata tgacccgtaa ctggaagaac gccttcgtca cgcactttgt gggtggtggt   180
ggccgtgtcg ttcaggtggc gaatgtgaac tatgttagct ggggtgcggg tcagtacgcc   240
aattcctaca gctacgcgca ggtcgaactg tgtcgtacga gcaacgccac gacgtttaag   300
aaggactatg aagtatactg ccaattgctg gtggatctgg cgaagaaagc gggcatcccg   360
attacgctgg atagcggtag caaaaccagc gacaaaggta ttaagtcgca caagtgggtg   420
gcggataaac tgggtggtac tacccatcag gacccgtacg catacctgag cagctggggc   480
atcagcaagg cgcaattcgc atccgacttg gcgaaagtta gcggcggtgg caataccggc   540
acggctccgc ctaaaccgag cactccagcc cctaagccaa gcaccccgtc taccaacctg   600
gacaagctgg gcctggtgga ttacatgaat gcgaagaaaa tggacagctc gtacagcaat   660
cgcgataagc tggcaaaaca gtacggtatc gcgaactatt ccggcaccgc tagccagaat   720
accaccctgc tgagcaagat caagggtggt gctccgaagc cgagcacccc ggcaccgaaa   780
ccgtctacga gcaccgcgaa aaagatttac tttccgccga taaaggtaa ctggagcgtt   840
tatccgacga acaaagcgcc ggtcaaagcg aatgcaattg gtgcaattaa cccgaccaag   900
ttcggtggcc tgacctatac cattcaaaaa gaccgtggca atggtgttta tgaaatccag   960
accgaccaat tcggtcgcgt tcaagtctat ggtgcgccgt ccacgggtgc cgtgatcaag  1020
aaataa                                                            1026
```